United States Patent
Lovley et al.

(10) Patent No.: US 9,074,198 B2
(45) Date of Patent: Jul. 7, 2015

(54) GEOBACTERACEAE STRAINS AND METHODS

(75) Inventors: Derek R. Lovley, Leyden, MA (US); Kelly P. Nevin, Amherst, MA (US); Hana Yi, Seoul (KR)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 739 days.

(21) Appl. No.: 12/789,294

(22) Filed: May 27, 2010

(65) Prior Publication Data

US 2010/0304189 A1    Dec. 2, 2010

Related U.S. Application Data

(60) Provisional application No. 61/181,460, filed on May 27, 2009.

(51) Int. Cl.
| | |
|---|---|
| C12N 1/00 | (2006.01) |
| C12N 1/20 | (2006.01) |
| C12N 1/36 | (2006.01) |
| C12N 15/01 | (2006.01) |
| H01M 8/16 | (2006.01) |

(52) U.S. Cl.
CPC C12N 1/20 (2013.01); C12N 15/01 (2013.01); H01M 8/16 (2013.01); Y02E 60/527 (2013.01)

(58) Field of Classification Search
CPC .......... Y02E 60/527; C12N 1/00; C12N 1/20; C12N 1/36
USPC ............ 429/401; 435/173.1, 173.8, 243, 245, 435/446
See application file for complete search history.

(56) References Cited

U.S. PATENT DOCUMENTS

2008/0286624 A1    11/2008    Lovley et al.
2010/0059436 A1    3/2010    Lovley et al.

OTHER PUBLICATIONS

Coppi et al, Appl. Environ. Microbiol. 67(7):3180-3187, 2001.*
Liu et al, Biosensors and Bioelectronics 24:1006-1011, 2008; available online Aug. 9, 2008.*
Kim et al, Appl. Microbiol. Biotechnol. 68: 23-30, 2005.*
Rabaey et al, Appl. Environ. Microbiol. 70(9): 5373-5382, 2004.*
Reguera et al, Appl. Environ. Microbiol. 72(11):7345-7348, 2006.*
Bond, D.R., D.R., Lovley. 2003. Electricity production by *Geobacter sulfurreducens* attached to electrodes. *Appl. Environ. Microbiol.* 69(3): 1548-1555.
Butler, J.E., N.D. Young, D.R., Lovley. 2010, Evolution of electron transfer out of the cell: comparative genomics of six Geobacter genomes, *BMC Genomics*, 11:40, http://www.biomedcentral.com/1471-2164/11/40.
Caccavo, Jr, F., D.J., et al., 1994, *Geobacter sulfurreducens* sp. nov., a hydrogen- and acetate-oxidizing dissimilatory metal-reducing microorganism. *Appl. Environ. Microbiol.* 60(10):3752-3759.
Cho, E.J., & Ellington, A.D., 2007, Optimization of the biological component of a bioelectrochemical cell. *Bioelectrochemistry.* 70:165-72. Epub Apr. 7, 2006.
Coates, J.D., et al., 1998, Carbohydrate-oxidation coupled to Fe(III) reduction, a novel form of anaerobic metabolism. *Anaerobe* 4: 277-282.
Coppi, M.V., et al., 2001, Development of a genetic system for *Geobacter sulfurreducens. Appl Environ Microbiol* 67: 3180-3187.
Franks, A.E & K.P. Nevin, 2010, Microbial Fuel Cells, A Current Review. *Energies* 3,899-919; doi:10.3390/en3050899.
Inoue, K., X. Qian, L. Morgado, B.-C. Kim, T. Mester, M. Izallalen, C.A. Salgueiro, Derek R. Lovley. 2010, Purification and Characterization of OmcZ, an Outer-1 Surface, Octaheme c-Type 2 Cytochrome Essential for Optimal Current Production by *Geobacter sulfurreducens, Appl. Environ. Microbiol.* 76(12): 3999-4007. doi:10.1128/AEM.00027-10 [Epub ahead of print Apr. 16, 2010.].
Izallalen, M., et al., 2008, *Geobacter sulfurreducens* strain engineered for increased rates of respiration, *Metab Eng.*; 10(5): 267-75.
Leang, C., M.V. Coppi, and D.R. Lovley, 2003, OmcB, a c-type polyheme cytochrome, involved in Fe(III) reduction in *Geobacter sulfurreducens. J. Bacteriol.* 185(7): 2096-2103.
Lovley, D.R. 2006. Bug juice: harvesting electricity with microorganisms, *Nature Reviews: Microbiology.* 4: 497-508.
Lovley, D.R & Nevin, K.P., 2008, Electricity Production with Electricigens, pp. 295-306 in Wall, J., et al., ed. *Bioenergy*, ASM Press, Washington, D.C.
Mehta, T., et al., 2005, Outer membrane c-type cytochromes required for Fe(III) and Mn(IV) oxide reduction in *Geobacter sulfurreducens. Appl Environ Microbiol* 71(12):8634-8641).
Methé, B.A., et al., 2003, Genome of *Geobacter sulfurreducens*: Metal Reduction in Subsurface Environments, *Science*, 302: 1967-1969.
Nevin, K.P., H. Richter, S.F. Covalla, J.P. Johnson, T.L. Woodard, A.L. Orloff, H. Jia, M. Zhang, and D.R. Lovley, 2008, Power output and columbic efficiencies from biofilms of *Geobacter sulfurreducens* comparable to mixed community microbial fuel cells, *Environmental Microbiology*, doi:10.1111/j.1462-2920.
Nevin KP, Kim B-C, Glaven RH, Johnson JP, Woodard TL, et al. (2009) Anode Biofilm Transcriptomics Reveals Outer Surface Components Essential for High Density Current Production in *Geobacter sulfurreducens* Fuel Cells. PLoS One 4(5): e5628. doi:10.1371/journal.pone.0005628.
Rabaey, K., N. Boon, S. D. Siciliano, M. Verhaege and Willy Verstraete 2004, Biofuel Cells Select for Microbial Consortia That Self-Mediate Electron Transfer, *Appl Environ Microbiol.* 70(9); 5373-5382.
Reguera, G., K.D. McCarthy, T. Mehta, J.S. Nicoll, M.T. Tuominen, and D.R. Lovley, 2005, Extracellular electron transfer via microbial nanowires, *Nature*, 435(7045): 1098-1101.

(Continued)

*Primary Examiner* — Kevin Hill
(74) *Attorney, Agent, or Firm* — Milstein Zhang & Wu LLC; Joseph B. Milstein

(57) ABSTRACT

Embodiments of the present invention provide a method of producing genetically modified strains of electricigenic microbes that are specifically adapted for the production of electrical current in microbial fuel cells, as well as strains produced by such methods and fuel cells using such strains. In preferred embodiments, the present invention provides genetically modified strains of *Geobacter sulfurreducens* and methods of using such strains.

11 Claims, 15 Drawing Sheets

(56) References Cited

OTHER PUBLICATIONS

Richter, H., K.P. Nevin, H. Jia, D.A. Lowy, D.R. Lovley and L.M. Tender. 2009. Cyclic voltammetry of biofilms of wild type and mutant *Geobacter sulfurreducens* on fuel cell anodes indicates possible roles of OmcB, OmcZ, type IV pili, and protons in extracellular electron transfer, *Energy Environ Sci* 2:506-516.

Risso, C., B.A. Methé, H. Elifantz, D.E. Holmes, and D.R. Lovley. 2008. Highly conserved genes in *Geobacter* species With expression patterns indicative of acetate limitation. *Microbiology* 154(Pt 9):2589-2599.

H. Yi, K. P. Nevin, B.-C. Kim, A.E. Franks, A. Klimes, L. M. Tender, D. R. Lovley, Selection of a variant of *Geobacter sulfurreducens* with enhanced capacity for current production in microbial fuel cells, Biosens Bioelectron. Aug. 15, 2009;24(12):3498-503. Epub May 14, 2009.

* cited by examiner

GEOBACTERACEAE STRAINS AND METHODS

RELATED APPLICATION

This application claims benefit of U.S. Provisional Patent Application 61/181,460, filed May 27, 2009, the entire contents of which are incorporated by reference for all purposes.

STATEMENT REGARDING FEDERALLY SPONSORED RESEARCH

Research carried out in connection with this invention was supported in part by the Office of Naval Research grant N00014-07-1-0966 and the Department of Energy Office of Biological and Environmental Research grant DE-FCO2-O2ER63446. Accordingly, the United States government may have certain rights in the invention.

FIELD OF THE INVENTION

The present invention relates generally to microorganisms capable of using organic compounds and application of such microorganisms for the production of electricity. Specific embodiments relate to genetically modified *Geobacter sulfurreducens* strains useful in microbial fuel cell applications.

BACKGROUND OF THE INVENTION

Microbial fuel cells offer the prospect of harvesting electricity from organic waste and renewable biomass. These are attractive sources of energy because they are 'carbon-neutral'; the oxidation of the organic matter only releases recently fixed carbon back into the atmosphere microbial fuel cells could fill a niche that is significantly different from that of the better known abiotic hydrogen- and methanol-driven fuel cells. However, microbial fuel cells do not require fuels that are toxic or explosive or expensive catalysts. Microbial fuel cells can oxidize a diverse range of 'dirty' fuels that are often of little perceived value, such as organic waste and the organic matter in soils and sediments. See, e.g., Lovley, D. R., 2006, Bug juice: harvesting electricity with microorganisms, *Nature Reviews Microbiology*, 4: 497-508.

Electricigens are microbes that conserve energy to support growth by completely oxidizing organic compounds to carbon dioxide with direct electron transfer to the anodes of microbial fuel cells. Electricity production with electricigens is significantly different from that of other types of microorganisms. See, e.g., Lovley, D. R & Nevin, K. P., 2008, Electricity Production with Electricigens, pp. 295-306 in Wall, J., et al., ed. *Bioenergy*, ASM Press, Washington, D.C. Electricigens have the ability to oxidize organic compounds to carbon dioxide with an electrode serving as the sole electron acceptor, providing high coulombic efficiency that is not available with other microbes. Since electricigens conserve energy for maintenance and growth from electron transfer to anodes, electricigen-powered microbial fuel cells have long-term sustainability. Electricigen-based microbial fuel cells have been run for more than 2 years without a decline in power output.

The most heavily studied electricigens are in the family Geobacteraceae (Lovley, D. R., & K. P. Nevin, 2008. Chapter 23: Electricity production with electricigens. In J. Wall et al. (ed.), *Bioenergy*. ASM Press, Washington, D.C. pp. 295-306). *Desulfuromonas* species, found in marine sediments, and *Geobacter* species, found in freshwater sediments, have similar physiologies, oxidizing short-chain fatty acids to carbon dioxide with Fe(III) oxides serving as the electron acceptor. Geobacteraceae species that have been shown to oxidize acetate with an electrode serving as the sole electron acceptor include *Desulfuromonas acetoxidans*, *Geobacter metallireducens*, and *Geobacter sulfurreducens*.

Genetic engineering approaches to improve the efficiency of current production in microbial fuel cells by inducing increased rates of respiration in a *Geobacter sulfurreducens* strain did not result in more current in microbial fuel cells than that produced by wild-type cells (Izallalen, M., et al., 2008, *Geobacter sulfurreducens* strain engineered for increased rates of respiration, Metab Eng.; 10(5): 267-75). However, it has been found that genetically modified strains of electricigenic microbes that are specifically adapted for improved production of electrical current in microbial fuel cells can be selected and maintained.

SUMMARY OF THE INVENTION

The present invention provides a method of selecting genetically modified strains of electricigenic microbes that are specifically adapted for the production of electrical current in microbial fuel cells, as well as strains produced by such methods and fuel cells comprising such strains.

Preferred embodiments provide an isolated culture of a genetically modified strain of an electricigenic microbe selected from the group consisting of *Desulfuromonas acetoxidans, Geobacter metallireducens, Geobacter sulfurreducens,* or *Rhodoferax ferrireducens*. In particularly preferred embodiments, such an isolated culture comprises a genetically modified strain of *Geobacter sulfurreducens*. In preferred embodiments, the genetically modified strain of *Geobacter sulfurreducens* is strain KN400, strain A45, strain B39, strain C49 or strain D43. In particularly preferred embodiments, the strain is the strain deposited with the American Type Culture Collection (ATCC), P.O. Box 1549, Manassas, Va. 20108, U.S., under Accession No. PTA-10251.

In other aspects, preferred embodiments provide a microbial fuel cell comprising a housing having an anode chamber and a cathode chamber; an anode disposed in an anaerobic environment within the anode chamber and electrically connected to an anode terminal; at least one electricigenic microbe disposed in the anaerobic environment within the anode chamber; a cathode disposed in an aerobic environment within the cathode chamber and electrically connected to a cathode terminal; and a semi-permeable barrier that provides ionic communication between the anode chamber and the cathode chamber. Typically, both the anode chamber and the cathode chamber contain aqueous solutions that are in contact with the anode and the cathode, respectively. Suitable electricigenic microbes for use in such microbial fuel cells include is a genetically modified strain of a microbe selected from the group consisting of *Desulfuromonas acetoxidans, Geobacter metallireducens, Geobacter sulfurreducens,* or *Rhodoferax ferrireducens*. Preferably, the electricigenic microbe is a genetically modified strain of *Geobacter sulfurreducens*. More preferably, the genetically modified strain of *Geobacter sulfurreducens* is a strain selected from the group of strain KN400, strain A45, strain B39, strain C49 and strain D43 described herein. In particularly preferred embodiments, the electricigenic microbe is the strain deposited with the American Type Culture Collection, Manassas, Va. under Accession No. PTA-10251 (PCA: KN400).

Typically, an aqueous solution that comprises an organic compound that can be oxidized by the electricigenic microbe is in contact with the anode within the anode chamber. Suitable such organic compounds include acetate. In other embodiments, the aqueous solution can include waste water of household, agricultural or industrial origin.

In other aspects, preferred embodiments provide a method of producing an electrically adapted microbial strain comprising the steps of providing an aliquot of electricigenic microbial cells; providing a sterile microbial fuel cell having an anode, a cathode, an anode chamber in electrical communication through a proton exchange membrane with a cathode chamber and a suitable growth medium for the aliquot of electricigenic microbial cells; placing the aliquot of electricigenic microbial cells in the anode chamber of the microbial fuel cell; maintaining a selected potential difference between the anode and the cathode of the microbial fuel cell using a potentiostat; measuring the amplitude of the current flowing between the anode and the cathode; removing an aliquot of electricigenic microbial cells from the anode chamber when the current flowing between the anode and the cathode reaches a criterion current amplitude; and repeating these steps M times, where M is an integer from 5 to 50 inclusive, thereby producing an electrically adapted microbial strain.

Preferably, a microbial fuel cell for the practice of the method is a flow-through fuel cell that is not cathode limited. Preferably, the electricigenic microbial cells are selected from species of the family Geobacteraceae, preferably species of the genera *Desulfuromonas* or *Geobacter*. In certain embodiments, the selected potential difference that is maintained between the anode and the cathode of the microbial fuel cell using a potentiostat is about −400 mV. In other embodiments, a potential difference of about +300 mV is maintained between the anode and the cathode of the microbial fuel cell using a potentiostat. Typically, the criterion current amplitude is 10 mA.

DESCRIPTION OF PREFERRED EMBODIMENTS

Figure 1A:
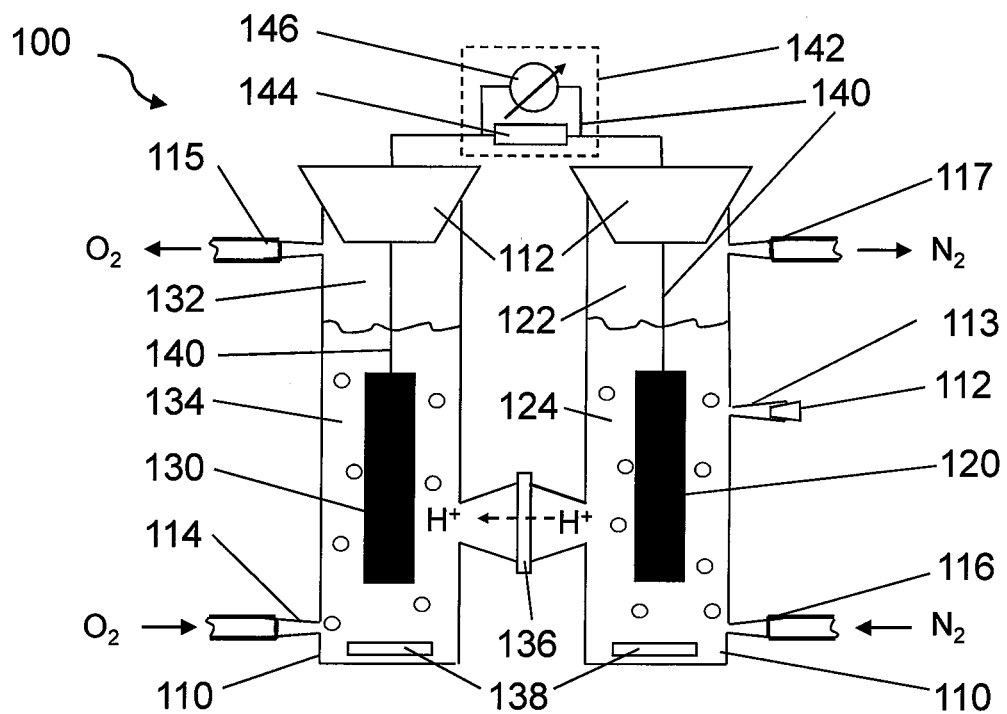
FIG. 1A is a schematic diagram of an "H-cell type" fuel cell suitable for use with the *Geobacter* strains of embodiments of the present invention.

*Geobacter sulfurreducens* produces current densities in microbial fuel cells that are among the highest known for pure cultures. The possibility of adapting this organism to produce even higher current densities was evaluated. A system in which a graphite anode was poised at −400 mV (versus Ag/AgCl) was inoculated with the wild-type strain of *G. sulfurreducens*, strain DL1. An isolate, designated strain KN400, was recovered from the biofilm after 5 months of growth on the electrode. KN400 was much more effective in current production than strain DL1. This was apparent with anodes poised at −400 mV, as well as in systems run in true fuel cell mode. KN400 had current (7.6 A/m$^2$) and power (3.9 W/m$^2$) densities that respectively were substantially higher than those of DL1 (1.4 A/m$^2$ and 0.5 W/m$^2$). On a per cell basis, KN400 was more effective in current production than DL1, requiring thinner biofilms to make equivalent current. The enhanced capacity for current production in KN400 was associated with a greater abundance of electrically conductive microbial nanowires than DL1 and lower internal resistance (0.015 Ω/m$^2$ versus 0.130 Ω/m$^2$) and mass transfer limitation in KN400 fuel cells. KN400 produced flagella, whereas DL1 does not. Surprisingly, KN400 had a lower level of outer-surface c-type cytochromes than DL1. KN400 also had a greater propensity to form biofilms on glass or graphite than DL1, even when growing with the soluble electron acceptor, fumarate.

While *Geobacter* species are the most effective microorganisms known for converting organic compounds to electricity in microbial fuel cells, their capacity for current production is probably a fortuitous benefit of their capacity to reduce other extracellular electron acceptors, such as Fe(III) oxides. There has been no known previous evolutionary pressure on *Geobacter* species to transfer electrons to electrodes. The optimal physiology for power production, i.e. the ability to rapidly oxidize a high concentration of electron donor, is a physiological characteristic that is unlikely to be subject to selection in the sedimentary environments in which *Geobacter* species are naturally found.

*G. sulfurreducens* strain PCA$^T$ (Caccavo, Jr, F., D. J., et al., 1994, Geobacter sulfurreducens sp. nov., a hydrogen- and acetate-oxidizing dissimilatory metal-reducing microorganism. *Appl. Environ. Microbiol.* 60(10):3752-3759; Methé, B. A., et al., 2003, Genome of *Geobacter sulfurreducens*: Metal Reduction in Subsurface Environments, *Science*, 302: 1967-1969) was routinely cultured under anaerobic conditions with acetate (10 mM) as the electron donor and fumarate (40 mM) as the electron acceptor, as previously described (Coppi, M. V., et al., 2001, Development of a genetic system for *Geobacter sulfurreducens*. *Appl Environ Microbiol* 67: 3180-3187).

In order to determine if the current output of *Geobacter sulfurreducens* in a fuel cell could be increased with selective environmental pressure, *G. sulfurreducens* was grown on the anodes of microbial fuel cells in a medium that had acetate as the electron donor. When the current production in a microbial fuel cell reached about 66% of the expected maximum, typically about 10 mA, generally late in log phase, a sample of bacteria was taken from the biofilm on the anode, and transferred by needle to the anode in a fresh fuel cell. In preferred embodiments of fuel cells, the suitable current production for transfer was about 10 mA.

After 15-20 such transfers, adaptive responses were observed in several characteristics that were apparently under evolutionary control. The characteristics became more evident as the procedure reached 40-50 transfers. First, the lag period prior to the onset of significant current production shortened from 4-5 days to less than one day. Second, the growth rate on the anode doubled. Third, the overall current production in the fuel cells increased by as much as 600%. Most remarkably, this increased current was produced by far fewer cells.

While the wild type strain of *G. sulfurreducens* that was obtained from a culture collection required a thick biofilm to produce maximal current, similar biofilms are not seen with the strains that were evolved using embodiments of the method of the present invention. Thus, the current production per mg of cell protein was at least 30-fold higher in the evolved strains than with the culture-collection strain and continues to improve with time in culture. The genomes of these evolved strains have been sequenced to determine what beneficial mutations may be associated with this remarkable increase in current production capacity.

In preferred embodiments, a flow-through potentiostat system that was not cathode limited was used to adapt *Geobacter sulfurreducens* with a potentiostat fuel cell anode (+300 mV vs. Ag/AgCl) serving as electron acceptor. Transfers by needle were made in late log phase to subsequent fuel cells.

In certain embodiments the isolated bacterial cells of the Geobacteraceae are cells of *Geobacter sulfurreducens* strain KN400. In some embodiments, the Geobacteraceae strain is that deposited and identified as ATCC deposit PTA-10251.

A power source for enhancing electrical potential between an anode and cathode of a microbial fuel cell may be included. Power sources used for enhancing electrical potential are not limited, and may include, but are not limited to a grid current, a solar power source (e.g., solar cell), a water power source (e.g., a water turbine), a wind power source (e.g., wind turbine), a DC power source, an electrochemical power source (e.g., a chemical cell, a battery, a capacitor).

Electrodes included in a microbial fuel cell useful in the invention are electrically conductive. Exemplary conductive electrode materials include, but are not limited to, carbon paper, carbon cloth, carbon felt, carbon wool, carbon foam, graphite, porous graphite, graphite powder, a conductive polymer, a conductive metal, such as platinum, and combinations of any of these.

In some embodiments, a microbial fuel cell is used for powering environmental sensors. In other embodiments, a microbial fuel cell is used for powering electronic devices or electric vehicles. The present invention is illustrated by the following examples, which should not be construed as further limiting.

Example 1

Production of *Geobacter* Strains Having Increased Current Production

*Geobacter* strains having increased current production in microbial fuel cells were obtained by iterative transfers of *Geobacter sulfurreducens* cells grown in potentiostat fuel cells that were poised at ±300-400 mV with respect to a silver/silver chloride electrode. In preferred embodiments, at least about 40 to about 50 transfers were performed before characterizing the resulting strain. Typically, a transfer was made when current production in the fuel cell reached about 10 mV.

The wild type *G. sulfurreducens* strain DL1 (ATCC 51573, DSMZ 12127; Coppi, M. V., et al., 2001) was used. *G. sulfurreducens* was grown with 10 mM acetate as the electron donor in either 55 mM Fe(III) citrate freshwater medium (Coates, J. D., et al., 1998, Carbohydrate-oxidation coupled to Fe(III) reduction, a novel form of anaerobic metabolism. *Anaerobe* 4: 277-282) or with fumarate (40 mM) in NBAF medium (Coppi, M. V., et al., 2001) with resazurin omitted and with 1.3 mM Fe(II) chloride added.

Suitable fuel cells can be made, for example, by the methods known in the art. See, e.g., Nevin, K. P., et al., 2008, Power output and columbic efficiencies from biofilms of *Geobacter sulfurreducens* comparable to mixed community microbial fuel cells, *Environmental Microbiology*, doi: 10.1111/j.1462-2920.

One embodiment of an "H-cell type" fuel cell 100 is illustrated schematically in FIG. 1A, showing a fuel cell comprising first and second vessels 110 in communication through a proton exchange membrane 136, elastomeric seals 112, an anode 120 contained within an anode chamber 122 and immersed in an anode solution 124, a cathode 130 contained within a cathode chamber 132 and immersed in an cathode solution 134. A nitrogen inlet 116 and a nitrogen outlet 117 communicate with the anode chamber 122 to provide an anaerobic environment. In certain preferred embodiments, an oxygen inlet 114 and an oxygen outlet 115 communicate with the cathode chamber 122 to provide oxygen, e.g., from air. At least one sample port 113, appropriately closed by an elastomeric seal 112, provides access to the anode chamber 122. Magnetic stirring bars 138 in combination with external magnets provide for mixing of the anode solution 124 within the anode chamber 122 and the cathode solution 134 within the cathode chamber 122. In certain preferred embodiments, the first and second vessels 110 are the same, and a sample port 113 and corresponding seal 113 are thus provided for the cathode chamber 132 (not shown).

Electrical wiring 140 completes the circuit through the load 142. The load comprises an external resistance, here illustrated by a resistor 144, and, optionally, current measuring means such as a voltmeter 146 in parallel measuring the current as the voltage drop across the known resistor 144, or an ammeter in series with the resistor 144. Other current measuring means may include data loggers or computer measurement systems comprising a processor executing instructions in communication with memory and a display. Typically the value of the resistor 144 is selected based on an analysis of the power output at different resistances, and then choosing the resistance that yields the maximum power.

While "H-cell type" fuel cells are convenient for microbiological studies, they have characteristics that limit the amount of power that can be produced by these microbial fuel cells (e.g., about 14 mW/m$^2$, Lovley & Nevin, 2008). For example, the rate at which electrons can be transferred onto oxygen in H-cells can limit power production. The rate of electron transfer can be increased somewhat if Fe(III) cyanide is added to the cathode solution 134 as the oxidant, but such systems are still cathode limited. The cathode limitation can be overcome with a potentiostat, which poises the anode at a fixed potential and ensures that transfer of electrons is not limited by cathodic reactions. This improvement comes at the cost of an input of energy, so the addition of a potentiostat does not provide a true fuel cell, but rather an electrochemically controlled system appropriate for mimicking anode reactions under ideal conditions. With a potentiostat, current levels in H-cells can reach much higher levels (about 14 mA versus about 0.4 mA), and thus, potentiostat-controlled H-type-cells are typically run with a continuous input of medium in order to provide sufficient fuel. See Lovley & Nevin, 2008.

In order to develop true fuel cells that can run at higher power densities the "ministack" fuel cell system was used (See Nevin, et al., 2008, and US 2008/0286624A1). Differences between the ministack and the H-cell include a greatly reduced distance between the anode and cathode and a large membrane surface area relative to the anode and cathode chamber volumes. In order to overcome the limitation of the cathode, ministack anodes were made substantially smaller than the cathode. When the current density produced in a ministack fuel cell with the anode one-eighth the area of that of the cathode was as great as that of an anode poised by the potentiostat, the limiting factor in the ministack became bacterial electron production. After these design and cathode electrochemical limitations were removed, current and power densities of 4.56 A/m$^2$ and 1.88 W/m$^2$, respectively, at a nominal resistance of 560Ω were obtained. Further reduction of the anode volume resulted in power densities of 2.15 kW/m$^3$ at a nominal resistance of 200Ω.

Figure 1B:
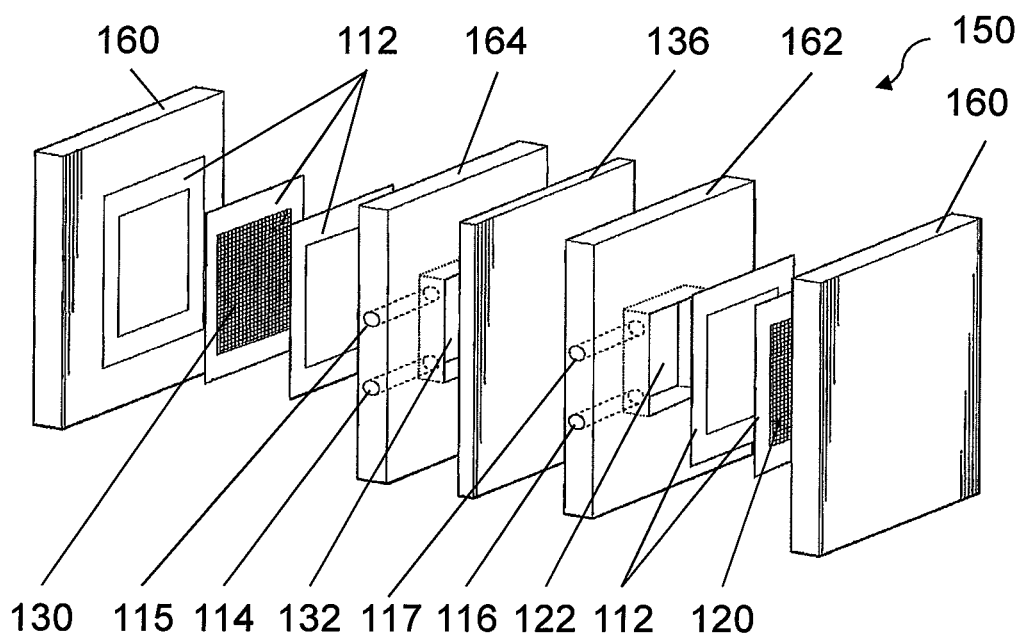
FIG. 1B is a schematic diagram of a "ministack" fuel cell suitable for use with the *Geobacter* strains of embodiments of the present invention.

One embodiment of a "ministack" fuel cell 150 is illustrated schematically in an exploded view in FIG. 1B, showing components of the fuel cell housing 160, elastomeric seals (i.e., gaskets) 112, an anode 120, an anode chamber frame 162 having nitrogen inlet 116 and outlet 117 ports, a proton exchange membrane 136, a cathode chamber frame 164 having oxygen inlet 114 and outlet 115 ports, and a cathode 130. The anode chamber 122 is the volume bounded by the housing 160, the proton exchange membrane 136, the anode chamber frame 162 and the elastomeric seals 112 and containing the anode 120. Similarly, cathode chamber 132 is the volume bounded by the housing 160, the proton exchange membrane 136, the cathode chamber frame 162 and the elastomeric seals 112 and containing the cathode 120. The external electrical circuitry, electrical components, and plumbing external to the ministack fuel cell are not shown in this schematic diagram.

In a preferred embodiment, a ministack fuel cell was constructed from two plastic methanol fuel cell stacks available from the Fuel Cell Store, Boulder Colorado, USA or from plastic or glass pieces of the same size and configuration. Anode 122 and cathode 132 chamber volumes were 7 ml (2.9 cm on each side and 0.85 cm deep). Gaskets were butyl rubber. The two chambers were separated with a cation selective membrane (Nafion 117, DuPont Fluoroproducts, Fayetteville, NC). In one embodiment, anodes (typically 2.54 cm×2.54 cm, but as small as 0.635 cm×0.635 cm) were graphite cloth (0.3 mm thick, grade GC-14, Electrolytica, Amherst, NY). In another embodiment, solid graphite anodes were 1.27 cm×0.635 cm×2 mm thick (grade G20, Graphite Engineering and Sales, Greenville, MI). Air-breathing cathodes were gas diffusion electrodes (2.54 cm×2.54 cm; 4.0 mg of Pt $cm^{-2}$, available from the Fuel Cell Store, Boulder Colorado, USA) hot-pressed to Nafion 117 membrane. In some instances, the cathode was graphite cloth (2.54 cm×2.54 cm) submerged in 50 mM ferricyanide, the reservoir was 200 ml, open to the air and re-circulated at a dilution rate of 0.85 $h^{-1}$.

All the solid parts of the fuel cells were sterilized before assembly with an ethylene oxide sterilizer (Anprolene gas sterilizer AN74i, Andersen Products, Inc., Haw River, N.C.) and the cation-selective membrane (Nafion 117) was autoclaved in distilled water. Alternatively, chambers were sterilized by UV irradiation; 10 min each side (Spectrolinker XL-1500 UV Crosslinker, Spectronics Corp., Westbury, N.Y.), then flushed with 1 liter of sterile water, filled with acetate+fumarate medium and connected to a 200 ml acetate+fumarate medium reservoir that re-circulated medium through the anode chamber at a dilution rate of 0.85 $h^{-1}$.

For selection for improved growth on an electrode, cells were grown anaerobically in an 'H-cell' as previously described (Bond, D. R., & Lovley, D. R., 2003, Electricity Production by *Geobacter sulfurreducens* Attached to Electrodes, *Appl. Environ. Microbiol.* 69 (3), 1548-1555). A graphite stick anode, which served as the sole electron acceptor in the system, was poised at a constant potential of −400 mV (versus Ag/AgCl electrode). Acetate (10 mM) was the sole electron donor. Once current production reached an apparent maximum, fresh medium was continuously provided to the anode chamber at a flow rate of 30 ml/hour.

After 5 months of incubation at −400 mV, a portion of the biofilm was aseptically scraped off the graphite stick under anaerobic conditions in an anaerobic glove bag. The scrapings were plated onto the acetate-fumarate medium described above, solidified with agar. Isolated colonies were picked, re-streaked onto agar plates, and isolated colonies picked and stored frozen for further study.

Fuel cells were operated in an anaerobic chamber to minimize oxygen diffusion into the system. The anode size was reduced by using a platinum wire (0.25 mm in diameter, $1 \times 10^{-5}$ $m^2$ surface area) or a small size graphite rod ($7.1 \times 10^{-6}$ $m^2$ surface area) instead of a graphite cloth electrode to help alleviate electrochemical limitations in the system. The cathode was graphite cloth (2.54 cm×2.54 cm). The anode was continuously supplied with fresh medium containing 10 mM acetate. The cathode medium contained 50 mM ferricyanide as the oxidant.

In order to provide enough cell material to further evaluate characteristics of cells growing in electrode biofilms, biofilms were grown on unpolished graphite stick electrodes (2.5 cm×7.6 cm×1.3 cm). The electrodes were poised at +300 mV (versus Ag/AgCl) and cells harvested when current reached 10 mA, which is about 70% of the maximum current density that strain DL1 produces in this system. In order to determine total cell numbers, the electrode biofilm biomasses were vigorously scraped with a razor blade into 9 ml of medium and vortexed. Cells in this slurry were fixed with the addition of 1 ml of 25% glutaraldehyde. Cells were disaggregated with sonication and were counted by epifluorescence microscopy. In order to determine total protein in biofilms scrapped from similar anodes, the scrapings were suspended in isotonic wash buffer and protein was measured with the bicinchoninic acid assay (Smith et al., 1985). To determine the amount of extracellular polysaccharide (EPS), biofilms were scraped from electrodes, suspended in 10 ml of Tris buffer (pH 7.5) and vortexed for 15 min at maximum speed to remove loosely bounded EPS from cells. Cells were removed with centrifugation and the supernatants were filtered (0.2 µm pore diameter) to remove any remaining cells. The EPS in the filtrate was further purified in stirred ultrafiltration cells with 30 kDa cut-off membranes. The retentates were collected and the EPS concentration was measured with the phenol-sulfuric acid assay using glucose as a standard.

Alternatively, to examine biofilms on carbon cloth anode surfaces, the fuel cells were disassembled and the anode was removed without touching its surface. Anodes were then dipped in freshwater medium to remove any loose cells or debris that was not part of the attached biofilm. Anode biofilms were fluorescently stained with the LIVE/DEAD BacLight Bacterial Viability Kit (L7012) (Molecular Probes, Eugene, Oreg.). Manufacturer's instructions were followed with the following exceptions: dyes were mixed in freshwater medium rather than bacterial suspension and, after the incubation step, samples were soaked again in freshwater media for 5 min to remove excess dye. After staining and while still wet, anodes were placed gently, so as not to disturb the biofilm, onto a few drops of an anti-fade agent (PROLONG®, P7481; Molecular Probes, Eugene, Oreg.) that had been added to the surface of a glass cover slip. Biofilm structures were examined with confocal laser scanning microscopy with a Zeiss LSM510 Meta inverted microscope equipped with a 10×, 25×, 40× or 63× objective lens. Two- and three-dimensional images were prepared and biofilm thicknesses were calculated using the Zeiss LSM Image Browser v.4.0.0.157. For each sample, average biofilm thickness was calculated by examining between two and seven fields of view, measuring the biofilm at three or more points along each observable carbon cloth fiber, for a total of more than 20 points.

The cytochrome content of cells scrapped from the anode was determined from dithionite-reduced minus air-oxidized difference spectra, as previously described (Caccavo et al., 1994). In order to evaluate outer-surface cytochromes, outer surface proteins were recovered as previously described (Mehta, T., et al., 2005, Outer membrane c-type cytochromes required for Fe(III) and Mn(IV) oxide reduction in *Geobacter sulfurreducens*. *Appl Environ Microbiol* 71(12):8634-8641). The presence of specific outer-surface c-type cytochromes was determined by separating proteins with tris-tricine denaturing polyacrylamide gel electrophoresis followed by heme-staining with N,N,N,N-tetramethylbenzidine as previously described (Leang, C., et al., 2003, OmcB, a c-type polyheme cytochrome, involved in Fe(III) reduction in *Geobacter sulfurreducens*. *J. Bacteria* 185(7): 2096-2103.). The concentration of enriched outer surface proteins was determined with the bicinchoninic acid method with bovine serum albumin as a standard (Smith, P. K., et al., 1985. *Anal. Biochem.* 150(1): 76-85).

In order to determine the amount of PilA protein in the biofilms immunoblots were probed with PilA-specific antiserum and immunoreactive bands were visualized with One-Step Western Kit (GeneScript Co., N.J.) according to the manufacturer's instructions.

Cells grown in acetate–fumarate medium attached to the surface of glass culture tubes. To evaluate this the medium was discarded when the cultures reached stationary phase. The remaining biomass attached to glass was stained with 1% crystal violet, and the cell-associated dye was then solubilized in ethanol and quantified by measuring the $OD_{580}$ of the dye-ethanol solution. Attachment to glass as well as graphite was examined by suspending glass or unpolished graphite coupons (12.7 mm×6.4 mm) in acetate–fumarate culture tubes. The coupons were removed once the culture reached stationary phase. Attached cells were stained with a green-fluorescent nucleic acid stain (SYTO9, S-34854, Molecular Probes, Eugene, Oreg.) and examined with confocal scanning laser microscopy.

When noted, the anode was poised at a selected voltage (e.g., −400 mV or +300 mV, versus Ag/AgCl) using a potentiostat (Amel Instruments, Milan, Italy or Gamry Potentiostat, Gamry Instruments, Warminster, Pa.). Current measurements for poised fuel cell experiments were obtained directly from potentiostat outputs every second with a Power Lab 4SP unit and CHART 5.0 (ADInstruments, Inc., Colorado Springs, Colo.) or Gamry Potentiostat with Multiplexer ECM8 and Gamry Framework 5.21 software (Gamry Instruments, Warminster, Pa.). Fuel cell voltage was measured across the resistor (560Ω) with a precision multimeter (Keithley, 2000, Keithley Instruments, Cleveland, Ohio). Current density-power relationships were determined by stepwise reduction of resistance between the anode and cathode.

The electron yield from acetate was measured in mature biofilms on anodes poised at +300 mV. The number of electrons that were transferred was calculated as previously described (Gregory et al., 2004). Acetate and other organic acids concentrations were determined with HPLC on a fast-acid column (Bio-Rad, Hercules, Calif.) with an eluent of 8 mM $H_2SO_4$ and UV detection at 210 nm.

Cell shape and appendages were examined with transmission electron contrast microscopy after staining with 1% uranyl acetate. Cellular motility was assessed from the diameter of colonies on 0.3% soft agar plates and confirmed with phase contrast microscopy of wet mounts. For biofilm analysis cells were stained to determine viability (LIVE/DEAD BacLight viability kit, Molecular Probes, Eugene, Oreg.) and examined by confocal scanning laser microscopy with a Leica TCS SP5 microscope. Leica LAS AF software (Leica, Microsystems GmbH) was used to create XYZ projections of vertical and horizontal sections and three-dimensional representations of the biofilms.

Example 2

Electrical Properties of *Geobacter sulfurreducens* Strains

In a preferred embodiment, *G. sulfurreducens* was inoculated into a system with a graphite stick anode poised at −400 mV (with respect to an Ag/AgCl electrode). *G. sulfurreducens* strain KN400 was isolated and characterized after about fifty transfers and growth in potentiostat fuel cells poised to −400 mV with respect to an Ag/AgCl electrode.

Cells within a sample scraped from the anode biofilm after 5 months of incubation produced colonies on anaerobic plates with medium that contained acetate as the electron donor and fumarate as the electron acceptor. Five individual colonies were selected for further study. Each of these colonies was re-streaked on acetate–fumarate plates and isolated colonies picked. All five of these lineages had 16S rRNA gene sequences that were 100% identical with the type strain of *G. sulfurreducens*. All five strains had similar phenotypic characteristics and are considered to be the same strain, which will be referred to here as *G. sulfurreducens* strain KN400.

Figure 2A:
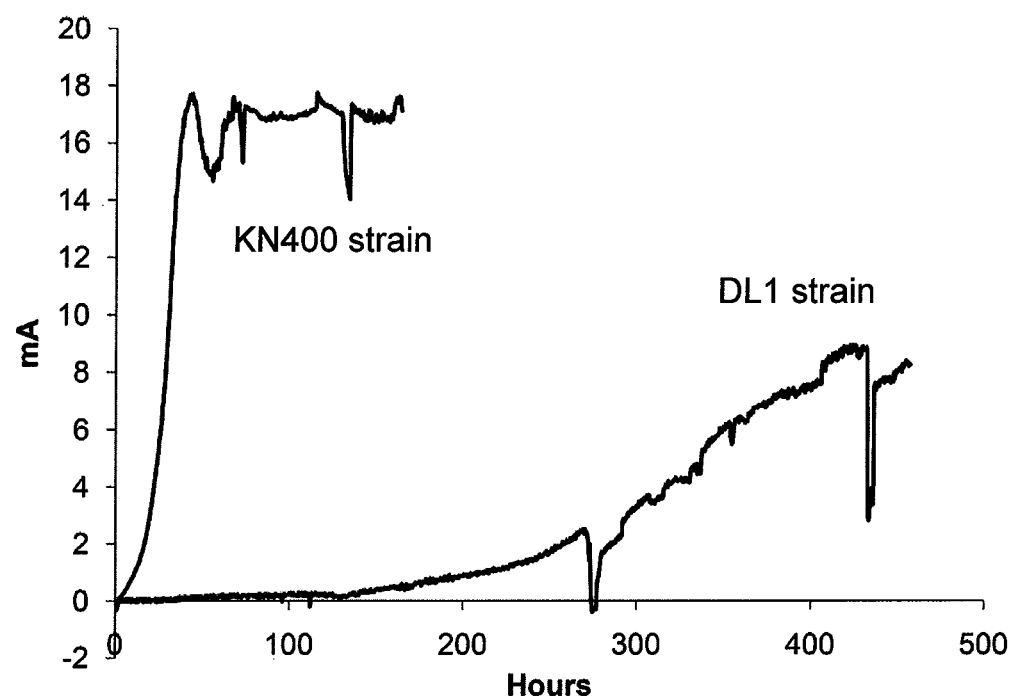
FIG. 2A is a graphical representation of current (mA) produced over time by strain KN400 and the DL1 wild type strain of *Geobacter sulfurreducens* in a poised fuel cell. The fuel cell was poised at −400 mV versus an Ag/AgCl reference electrode.

The phenotypic characteristics of the KN400 strain are compared to those of the wild type strain DL1 of *G. sulfurreducens* that served as the initial inoculum. In general, when *G. sulfurreducens* was inoculated into a system with a graphite stick anode poised at −400 mV (versus Ag/AgCl), the current produced increased to a maximum of about 14 mA within about 12 days and maintained this level of current output for over 24 months of incubation. A specific example is shown in FIG. 2A, which is a graphical representation of current (mA) produced over time by strain KN400 and the wild type DL1 strain of *G. sulfurreducens* in such a poised fuel cell. The current produced by strain KN400 reached 10 mA in about four days in culture, and peaked above 17 mA, while the current production of the wild type DL1 strain only reached 8 mA after more than 2.5 weeks. The results of a comparison of the current density performance of strain KN400 and the wild type DL1 strain of *G. sulfurreducens* using a graphite rod anode or a platinum rod anode showed that strain KN400 produced several fold higher current density (about three-fold to about five-fold) compared to the wild type DL1 strain with either a graphite rod anode or a platinum rod anode.

Figure 2B:
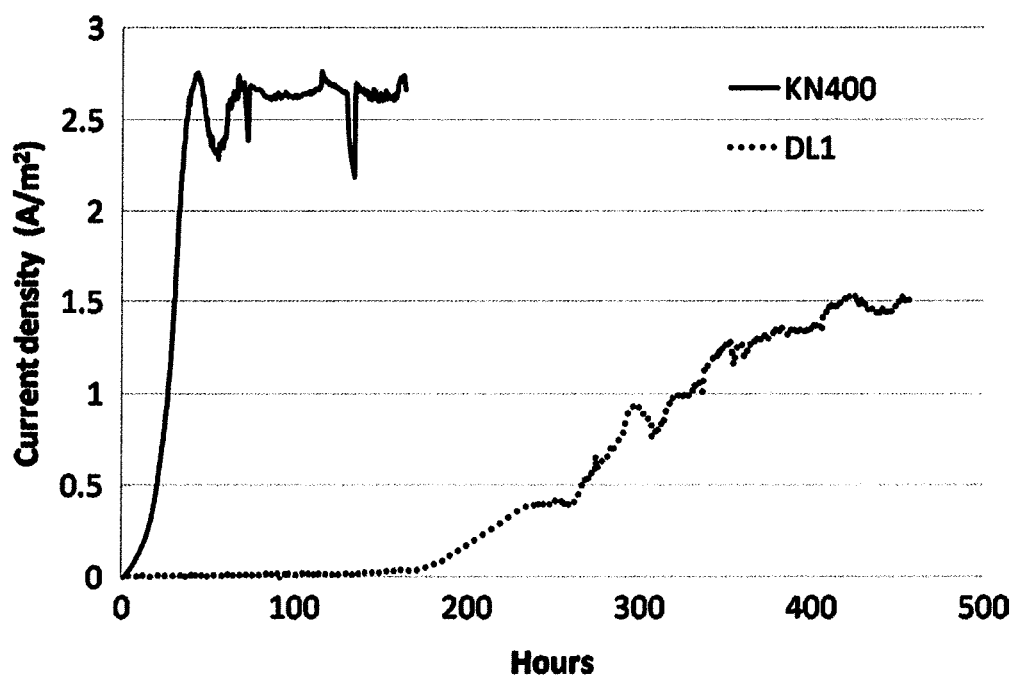
FIG. 2B is a graphical representation of current density (mA/m²) produced over time by strain KN400 and the DL1 wild type strain of *Geobacter sulfurreducens* in a poised fuel cell. The fuel cell was poised at −400 mV versus an Ag/AgCl reference electrode.

Current production of KN400 was tested in true microbial fuel cells, without artificial poising of the anode, in order to evaluate current production under conditions that have relevance to most microbial fuel cell applications. The anode was made of platinum wire in order to provide a smooth surface so that calculations of current and power densities reflect actual surface area, not nominal surface area of materials that have additional surface area well beyond that calculated from the anode geometry, such as unpolished graphite or graphite fibers. The surface area of the anode was maintained much smaller than that of the cathode in order to prevent the rate of reaction at the cathode from limiting current production. With an external resistance of 560Ω, the KN400 strain produced current much more rapidly and generated much higher maximum current densities than the DL1 wild-type strain (FIG. 2B). FIG. 2B is a graphical representation of current density ($A/m^2$) produced over time by strain KN400 and wild type DL1 strain of *G. sulfurreducens* in such a poised fuel cell. Maximum current densities for the KN400 strain were 7.4±0.1 (mean±standard deviation; n=3) $A/m^2$ compared to 1.4±0.2 $A/m^2$ for the DL1 wild-type strain in these microbial fuel cells.

TABLE 1

Current Production in True Fuel Cell System

| Anode size (Anode:Cathode) | Strain | Current (mA) | Current Density ($A/m^2$) |
|---|---|---|---|
| 1:8 | KN400 | 0.80 | 4.91 |
|  | DL1 | 0.71 | 4.36 |

TABLE 1-continued

Current Production in True Fuel Cell System

| Anode size (Anode:Cathode) | Strain | Current (mA) | Current Density (A/m$^2$) |
|---|---|---|---|
| 1:16 | KN400 | 0.78 | 9.38 |
|  | DL1 | 0.39 | 4.69 |

Figure 3A:
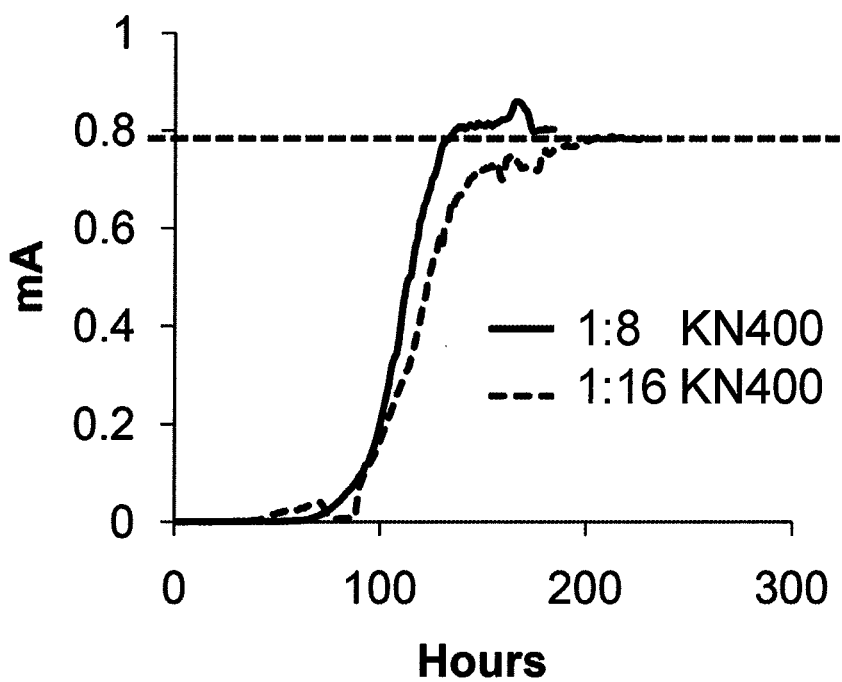
FIG. 3A is a graphical representation of the effect of the relative size of the anode (expressed as the ratio of the area of the anode to the area of the cathode) on current (mA) production over time by strain KN400 of *Geobacter sulfurreducens* in fuel cells having a two-fold difference of relative anode area, 1:8 versus 1:16.

FIG. 3A is a graphical representation of the effect of the relative size of the anode (expressed as the ratio of the area of the anode to the area of the cathode) on current (mA) production over time by strain KN400 of *G. sulfurreducens* in fuel cells having a two-fold difference of the relative anode area, 1:8 versus 1:16, where the dashed line indicates the limitation of the ministack fuel cell system.

Additional microbial fuel cell studies were carried out with anodes comprised of solid, unpolished graphite because graphite is so commonly used as an anode material. When nominal surface area was considered, both strains produced more current on the graphite anode than on the platinum anode, 9.7±0.7 and 3.5±0.4 A/m$^2$ for the KN400 and the DL1 strains, respectively. The higher current on the graphite was presumably due to higher actual surface area on the unpolished graphite. The maximum current production of DL1 with the solid graphite compared well with previous current densities reported for solid graphite, but was lower than the current (4.56 A/m$^2$) previously reported with carbon fiber anodes (Nevin et al., 2008), which have significantly more actual surface area for microbial colonization than suggested by nominal geometrical surface area. These differences emphasize the difficulties in comparing current densities between studies that use different anode materials. However, the results demonstrated that in side-by-side comparisons, the KN400 strain produced significantly more current than the DL1 wild-type strain.

Figure 3B:
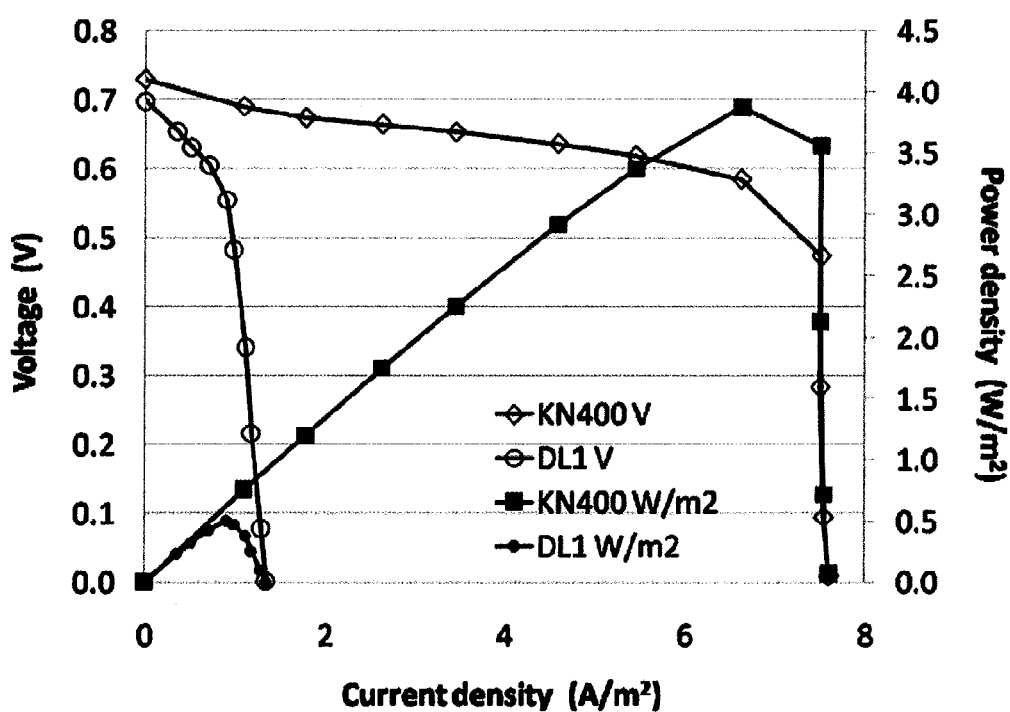
FIG. 3B is a graphical representation of the current-voltage and current-power densities relationships for the KN400 strain and the DL1 wild type strain in microbial fuel cells with platinum wire anodes.

Further analysis of electron transfer over a range of external resistances further demonstrated the superior capabilities of the KN400 strain (FIG. 3B). The calculated internal resistance of the KN400 microbial fuel cells (0.015 Ω/m$^2$; linear region between 1-6 mA/m$^2$; r$^2$=0.99) was much lower than the internal resistance for the DL1 microbial fuel cells (0.130 Ω/m$^2$; linear region between 0-1.5 mA/m$^2$; r$^2$=0.99). The internal resistance reflects the resistance to the flow of charge compensating ions between the anode and cathode that is required for electron flow in the external circuit. Since the sluggish movement of protons out of *G. sulfurreducens* anode biofilms has been suggested to limit current production, the lower internal resistance of the KN400 microbial fuel cells could be due to better movement of protons through KN400 biofilms.

The rapid decline in voltage at higher current (FIG. 3B) is believed to be due to mass transfer limitations. The KN400 strain was capable of producing higher currents (FIG. 3B, open diamonds) prior to experiencing mass transfer limitation than the DL1 wild-type strain (FIG. 3B, open circles). The observed substantial differences in mass transfer limitations between the KN400 strain and the DL1 wild-type strain suggest that there are fundamental differences in the physiology of the strains. Mass transfer limitations on current productions in *G. sulfurreducens* biofilms could be dependent on the rate of acetate uptake per cell, the number of microorganisms actively contributing to current production in the anode biofilm, and the rate of electron transfer for the microbes.

Power density is the product of current density and voltage. The net effect of decreased internal resistance and increased mass transfer-limited current resulted in a several-fold greater maximum power density for the KN400 strain compared to the DL1 wild-type strain (FIG. 3B, filled symbols).

Previous studies with strain DL1 have suggested a direct correlation between the amount of anode biomass and current production. In the present studies, at maximum current levels on the platinum anodes, the KN400 strain produced homogeneous biofilms 25.6±6.5 μm thick, while the DL1 wild-type strain produced biofilms that were 10.6±1.9 μm thick and less homogeneous. However, this relative difference in biofilm thickness was substantially less than the relative difference in current density (FIG. 4B). On graphite anodes, the biofilms of the KN400 strain and the DL1 wild-type strain were both about 25 μm thick, despite the greater current output of the KN400 strain (FIG. 4A), indicating that the greater current production with KN400 could not be attributed to thicker anode biofilms on graphite anodes.

In order to more definitively evaluate the differences in current producing capacities of the two strains under highly controlled, identical conditions, they were grown on graphite stick electrodes poised at +300 mV, which were harvested when the strains reached a current of 10 mA. This criterion, about 70% of the maximum current density that strain DL1 produces in such a system, was chosen to analyze the cells in the active growth phase on the anode, and diminish the possibility of moribund biomass accumulating in the biofilm, and thus be a more accurate measure of the current per cell ratio. Under these conditions, the KN400 biofilms were 9.3±0.7 μm thick, and the DL1 biofilms were 16.8±3.8 μm thick, showing that less KN400 biomass was required to make an equivalent amount of current. Furthermore, the DL1 biofilm completely covered the graphite surface with a dense under-layer and with pillar structures forming on top of this layer. The KN400 biofilm did not cover the entire surface, and there were small vertical spaces between biofilm columns.

Similar biofilms were scraped from the anodes and analyzed for total protein, and cell numbers. Compared to the DL1 biofilms, the KN400 biofilms had about half the cell protein (26.8±1.4 μg/cm$^2$ of anode area versus 57.1±1.6 μg/cm$^2$) and 5-fold fewer cells (2.0×10$^8$±0.3 versus 9.9×10$^8$±0.9 cells/cm$^2$). These results showed that the KN400 strain is much more effective than DL1 in current production on a per cell basis. Similarly, the columbic yield with the KN400 strain in this system was 84.8±0.8% compared to 70.1±2.3% for the DL1 wild-type strain, indicating that the KN400 strain directed relatively more electron flow to current production than to cell synthesis.

Figure 4A:
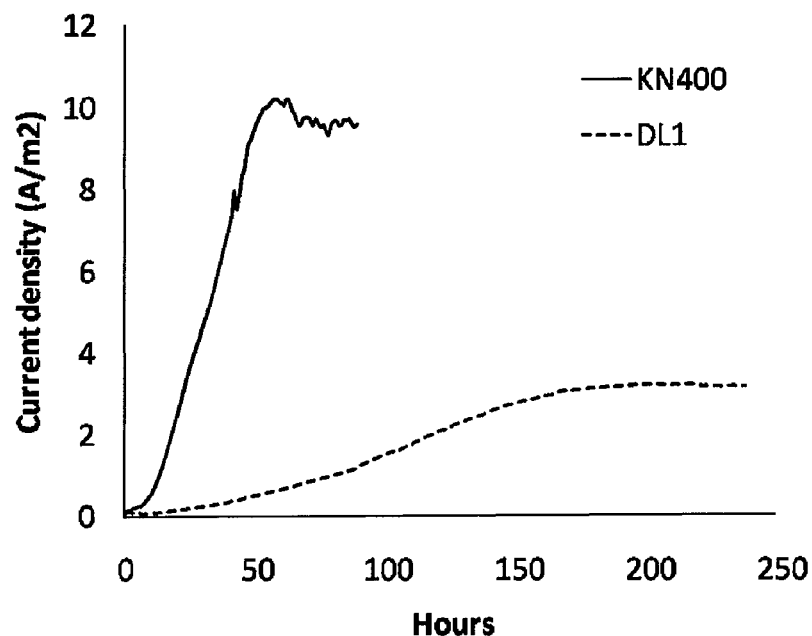
FIG. 4A is a graphical representation of the results of a study comparing the current density (A/m²) produced by strain KN400 and the DL1 wild type strain using a graphite rod anode.
Figure 4B:
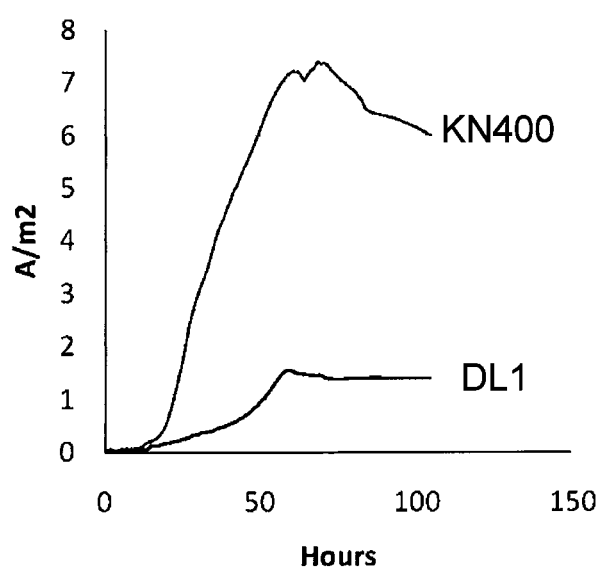
FIG. 4B is a graphical representation of the results of a study comparing the current density (A/m²) produced by strain KN400 and the DL1 wild type strain using a platinum wire anode.

FIG. 4A is a graphical representation of the results of a study comparing the current density (A/m2) produced by strain KN400 and the DL1 wild type strain using a graphite rod anode. Strain KN400 showed a faster increase and a higher final value of current density than the DL1 wild type strain. The same qualitative result can be seen in FIG. 4B. FIG. 4B is a graphical representation of the results of a study comparing the current density (A/m2) produced by strain KN400 and the DL1 wild type strain using a platinum wire anode.

Figure 5:
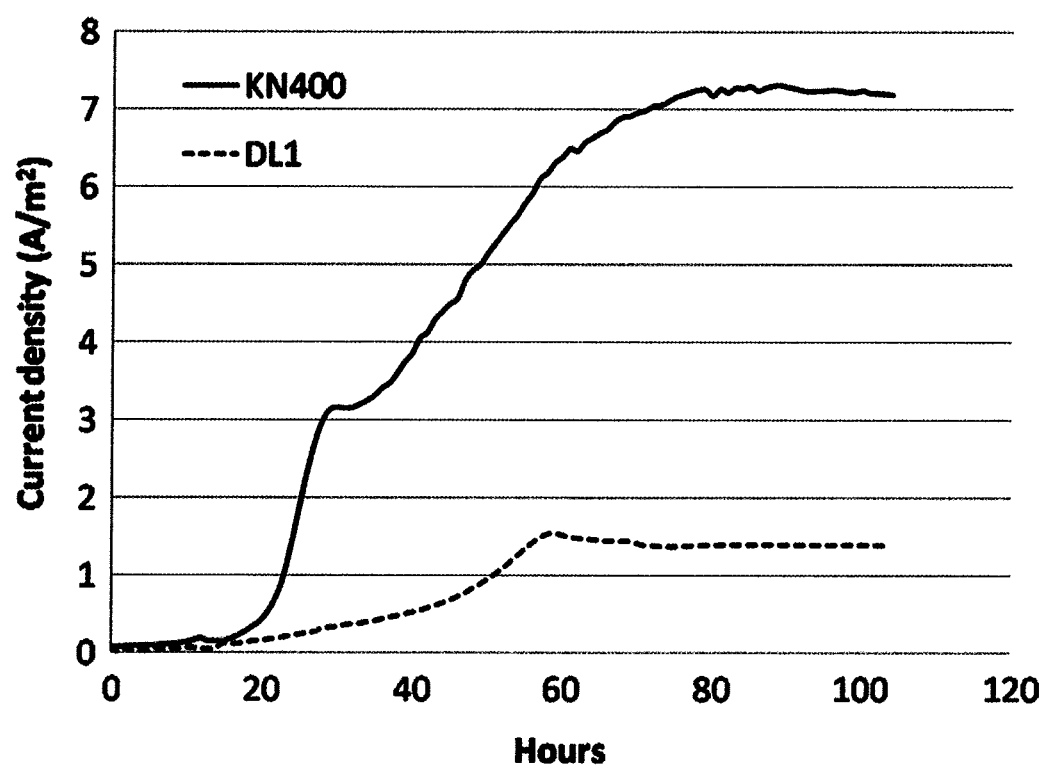
FIG. 5 is a graphical representation of the results of a study comparing the current density (A/m²) produced by strain KN400 and the DL1 wild type strain in fuel cell mode using a platinum wire anode and an external resistance of 560Ω.

FIG. 5 is a graphical representation of the results of a study comparing the current density (A/m2) produced by strain KN400 and the DL1 wild type strain in fuel cell mode using a platinum wire anode and an external resistance of 560Ω.

Figure 6:
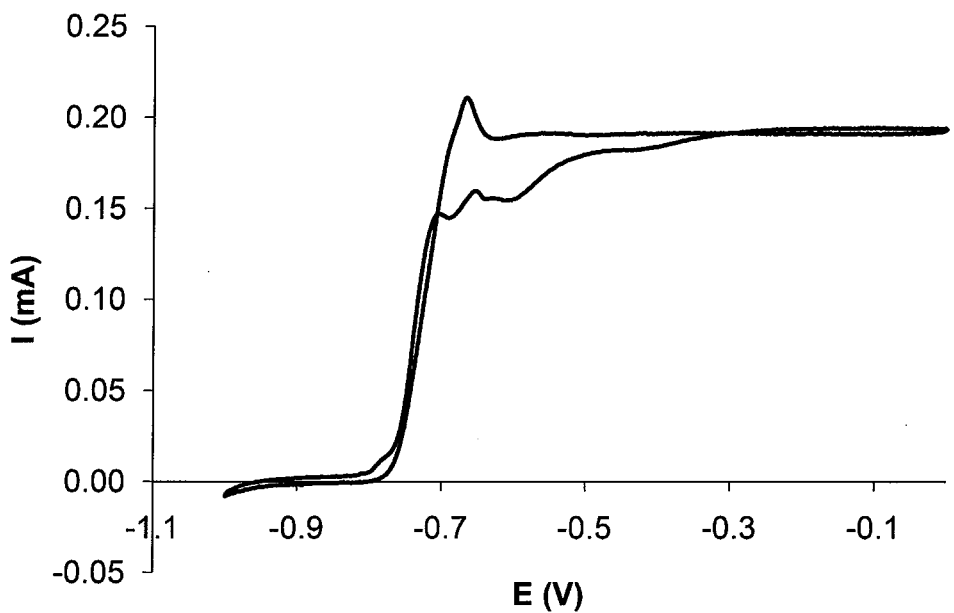
FIG. 6 is a graphical representation of the results of an electrochemical analysis in which a cyclic voltammetric curve is produced using a scan rate of 2 mV/second, where strain KN400 was found to have a midpoint potential of −230 mV (referenced to a $H_2$ electrode) and the DL1 wild type strain was found to have a midpoint potential of −150 mV (referenced to a $H_2$ electrode).

The current-voltage characteristics of a microbial fuel cell containing strain KN400 were compared to those of a microbial fuel cell containing the DL1 wild type strain. FIG. 6 is a graphical representation of the results of an electrochemical analysis in which a cyclic voltammetric curve is produced using a scan rate of 2 mV/second, where strain KN400 was found to have a midpoint potential of 230 mV (referenced to a H2 electrode) and the DL1 wild type strain was found to have a midpoint potential of 150 mV (referenced to a H2 electrode).

Example 3

Physiological Characteristics and Growth

Figure 7:
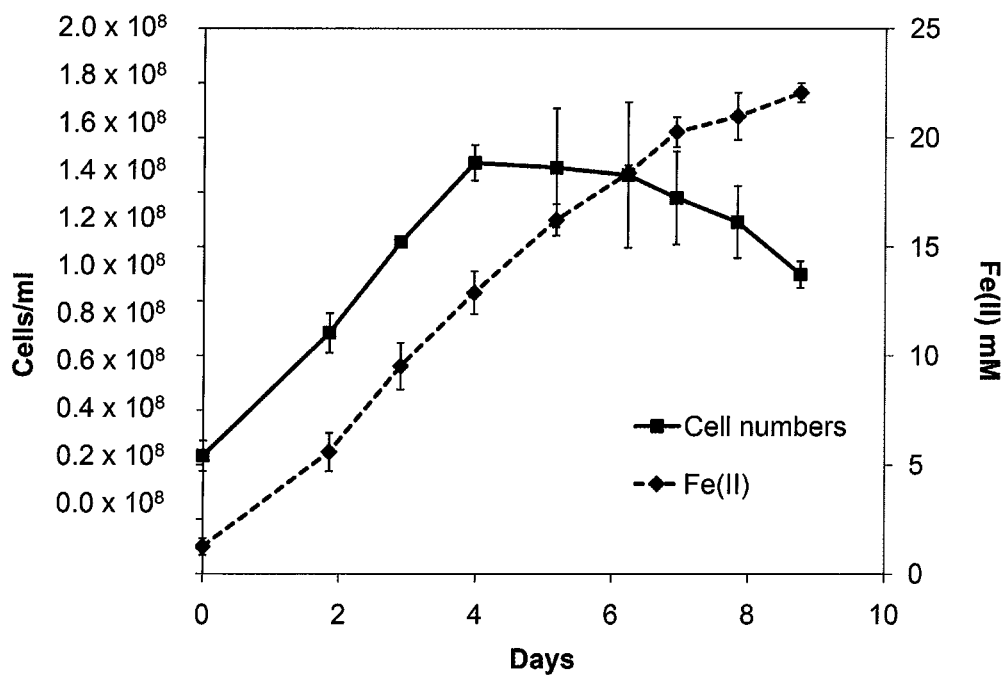
FIG. 7 is a graphical representation of the results of a study of Fe(III) oxide reduction where the cell density (filled squares, cells/ml) and Fe(II) concentration (filed diamonds, mM) are plotted as a function of days in culture. The data points represent the averages of triplicate measurements and the error bars represent ±1 standard deviation.

A study of the increase in cell density and the use of Fe(III) oxide as an electron acceptor in a fuel cell with the anode poised at +300 mV showed that the cell strain KN400 grew faster than those of the DL1 wild type under these conditions. FIG. 7 is a graphical representation of the results of a study of Fe(III) oxide reduction where the cell density (filled squares, cells/ml) and Fe(II) concentration (filed diamonds, mM) are plotted as a function of days in culture. The data points represent the averages of triplicate measurements and the error bars represent ±1 standard deviation.

Figure 8:
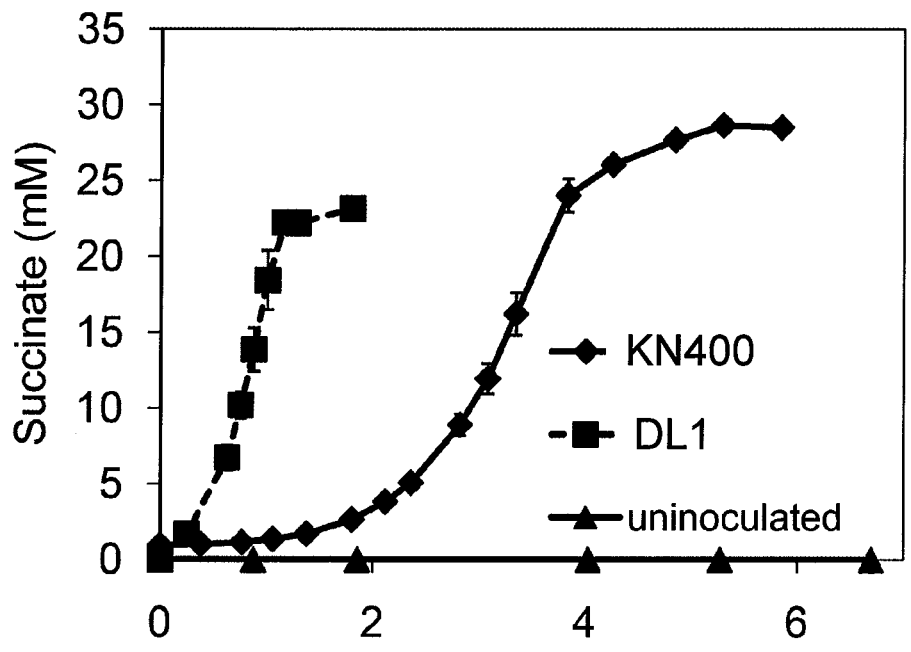
FIG. 8 is a graphical representation of the results of a study of the growth of strain KN400 (filled diamonds) and the DL1 wild type strain (filled squares) on media containing 40 mM fumarate, where the succinate concentration (mM) is plotted as a function of days in culture, and the filled triangles indicate the values obtained for the uninoculated medium control. The data points represent the averages of triplicate measurements and the error bars represent ±1 standard deviation.

Further characterization of the physiological characteristics of strain KN400 examined the growth of cells provided with the soluble electron acceptors fumarate or ferric citrate. FIG. 8 is a graphical representation of the results of a study of the growth of strain KN400 (filled diamonds) and the DL1 wild type strain (filled squares) on media containing 40 mM fumarate, where the succinate concentration (mM) is plotted as a function of days in culture, and the filled triangles indicate the values obtained for the uninoculated medium control. The data points represent the averages of triplicate measurements and the error bars represent ±1 standard deviation. The growth of strain KN400 on fumarate medium lagged behind the growth of the DL1 wild type strain by about two days.

Figure 9:
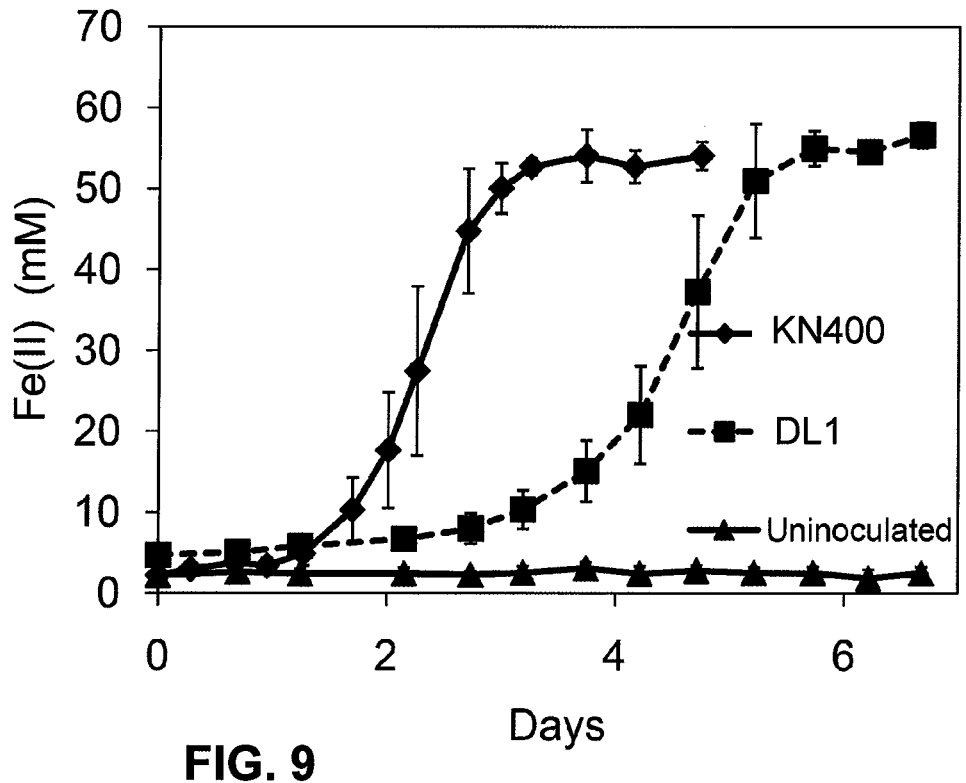
FIG. 9 is a graphical representation of the results of a study of the growth of strain KN400 (filled diamonds) and the DL1 wild type strain (filled squares) on media containing 55 mM ferric citrate, where the Fe(II) concentration (mM) is plotted as a function of days in culture, and the filled triangles indicate the values obtained for the uninoculated medium control. The data points represent the averages of triplicate measurements and the error bars represent ±1 standard deviation.

FIG. 9 is a graphical representation of the results of a study of the growth of strain KN400 (filled diamonds) and the DL1 wild type strain (filled squares) on media containing 55 mM ferric citrate, where the Fe(II) concentration (mM) is plotted as a function of days in culture, and the filled triangles indicate the values obtained for the uninoculated medium control. The data points represent the averages of triplicate measurements and the error bars represent ±1 standard deviation. In contrast to the results shown in FIG. 8, the growth of the DL1 wild type strain on ferric citrate medium lagged behind the growth of strain KN400 by about two days.

Example 4

Methods of Making *Geobacter sulfurreducens* Strains

Additional strains having similar characteristics have been produced using variations of the potential imposed by the potentiostat and the number of transfers before the isolation of the strain. Surprisingly, strains with improved current production were produced using potentiostats poised at +300 mV or at −400 mV.

TABLE 2

Methods of Producing Strains With Improved Characteristics

| Strain | Poise (referenced to Ag/AgCl electrode) | Number of Transfers Before Isolation Of Strain |
|---|---|---|
| KN400 | −400 mV | 50 |
| A | +300 mV | 45 |
| B | | 39 |
| C | | 49 |
| D | | 43 |
| E, F, G | −400 mV | 50 |

After 45 transfers of replicate A (A45), the process was terminated and the characteristics of the resulting strain were examined. Replicate B (B39) was terminated after 39 transfers; replicate C(C49) was terminated after 49 transfers; and replicate D (D43) was terminated after 43 transfers.

The characteristics that were examined included cell growth in non-cathode limited ministacks, growth in poised potential fuel cell systems, the biofilm structure of bacteria grown in ministacks and poised potential systems, electrochemical characteristics, cytochrome content, growth utilizing other electron acceptors, outer surface proteins, motility and cellular appendages.

Figure 10:
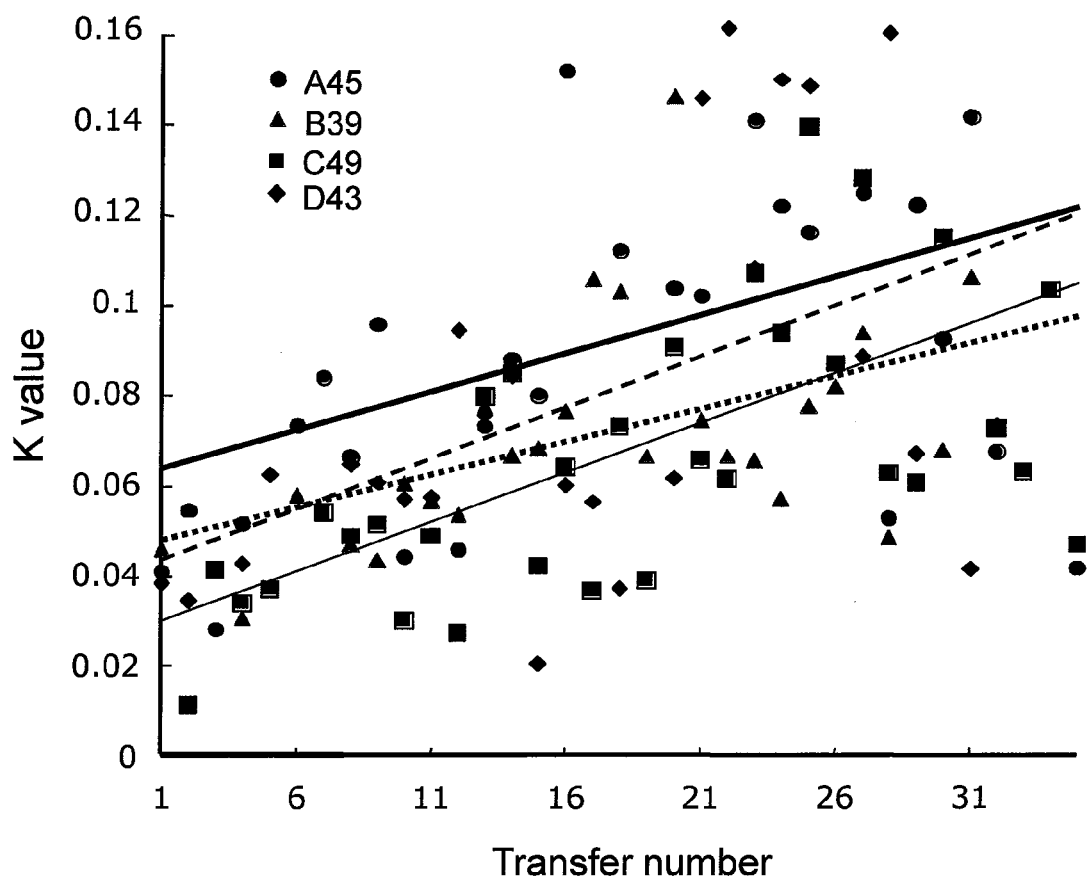
FIG. 10 is a graphical representation of the results studies showing an increase of growth rates with successive transfers on electrodes showing linear regression lines for four strains replicate A45 (filled circles, thick line), replicate B39 (filled triangles, dashed line), replicate C49 (filled squares, thin line), and replicate D43 (filled diamonds, dotted line).

It was found that the growth rate increased with subsequent transfers. FIG. 10 is a graphical representation of the results studies showing an increase of growth rates with successive transfers on electrodes showing linear regression lines for four strains replicate A45 (filled circles, thick line), replicate B39 (filled triangles, dashed line), replicate C49 (filled squares, thin line), and replicate D43 (filled diamonds, dotted line).

The characteristics that were studied included growth in non-cathode limited ministacks, growth in poised potential fuel cell systems, biofilm structure found in the ministack systems and poised potential systems, electrochemical characteristics, cytochrome content, growth utilizing other electron acceptors, outer surface proteins, motility and cellular appendages The biofilms that were formed on the anode by all four replicates were thinner than the biofilms that were produced by the DL1 wild type strain at the same level of current production (10 mA, in late log growth phase). For example, an examination using confocal microscopy showed that a biofilm of the replicate B39 strain was thick and coated the fibers of the carbon cloth anode. The biofilm was a maximum of 50 μm thick across the fiber, similar to maximal pillar height in poised potential systems. In comparison, the biofilm produced by the DL1 wild type strain of *G. sulfurreducens* was much thinner than that of the adapted replicate B39 strain. Similarly, the biofilm of the C49 strain was thick and coated the fibers of the carbon cloth anode like the biofilms of the other electrode adapted strains.

Figure 11:
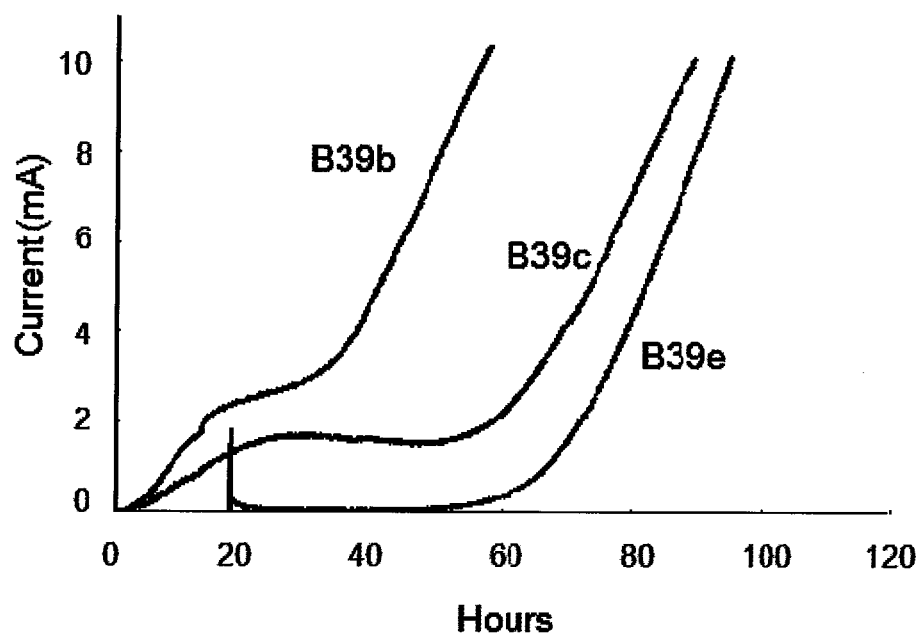
FIG. 11 is a graphical representation of the current (mA) produced in a fuel cell over time by three samples (B39b, B39c, and B39e) of the B39 strain of *Geobacter sulfurreducens* harvested at 10 mA. The fuel cell was poised at +300 mV referenced to an Ag/AgCl electrode.

FIG. 11 is a graphical representation of the current (mA) produced in a fuel cell over time by three samples (B39b, B39c, and B39e) of the B39 strain of *Geobacter* sulfurreducens harvested at 10 mA. The fuel cell was poised at +300 mV referenced to a Ag/AgCl electrode.

Figure 12:
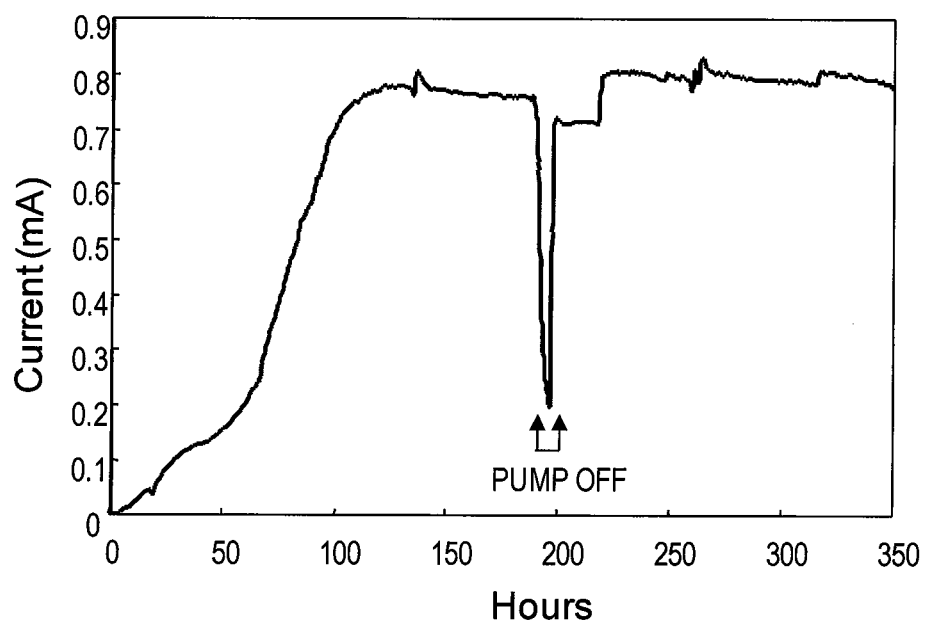
FIG. 12 is a graphical representation of the current (mA) produced in a ministack fuel cell system over time by replicate B39 strain of *Geobacter sulfurreducens* harvested at 10 mA. Turning off the pump that circulated the medium produced a decrease in current production (arrows).

FIG. 12 is a graphical representation of the current (mA) produced in a ministack fuel cell system over time by replicate B39 strain of *Geobacter sulfurreducens* harvested at 10 mA. Turning off the pump that circulated the medium produced a decrease in current production (arrows).

Figure 13:
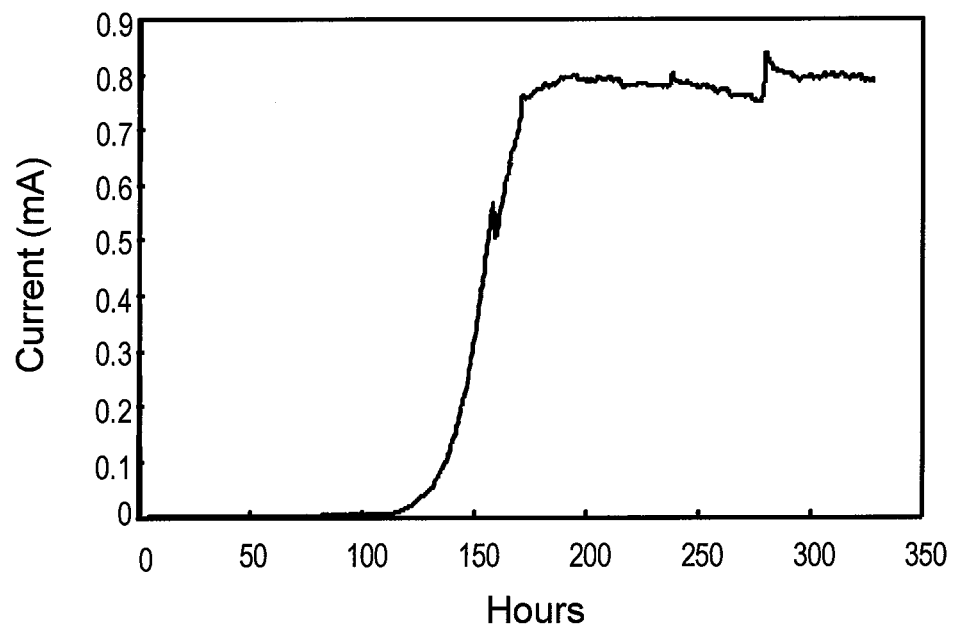
FIG. 13 is a graphical representation of the current (mA) produced in a ministack fuel cell system over time by replicate D43 strain of *Geobacter sulfurreducens*.

FIG. 13 is a graphical representation of the current (mA) produced in a ministack fuel cell system over time by replicate D43 strain of *Geobacter sulfurreducens*.

Figure 14:
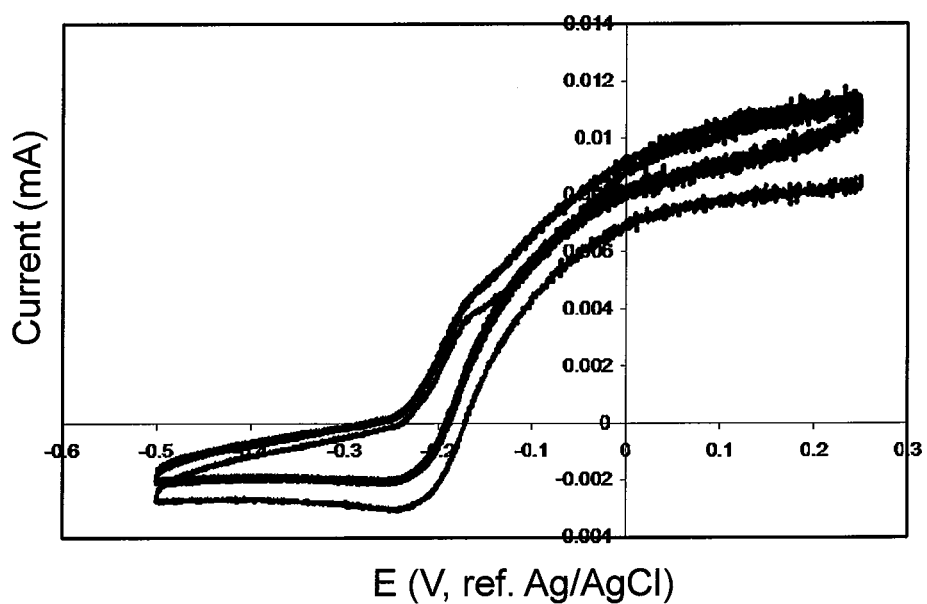
FIG. 14 is a graphical representation of the results of a current-voltage scan of replicate D43, where the potential is referenced to an Ag/AgCl electrode, and the ratio of the area of the anode to the area of the cathode was 1:16.

FIG. 14 is a graphical representation of the results of a current-voltage scan of replicate D43, where the potential is referenced to an Ag/AgCl electrode, and the ratio of the area of the anode to the area of the cathode was 1:16.

Example 5

Genomic Characterization

Figure 15:
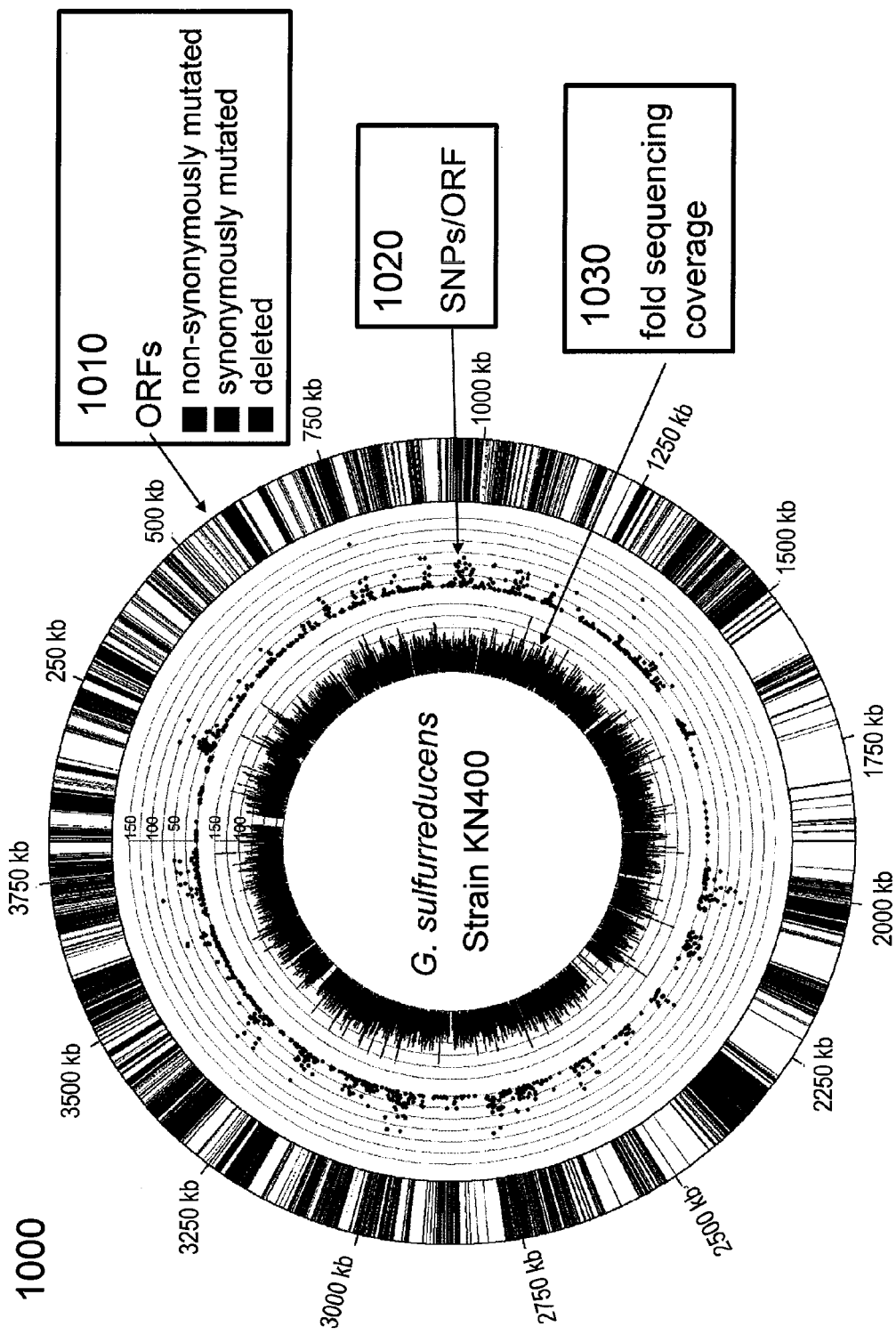
FIG. 15 is a graphical representation 1000 of the results of whole genome sequencing of the *Geobacter sulfurreducens* strain KN400 showing the positions (kb) of non-synonymously mutated, synonymously mutated and deleted open reading frames (ORFs) 1010 (outer band), the numbers of single nucleotide polymorphisms (SNPs) at positions in open reading frames in open reading frames (ORFs) 1020 (middle band) and the fold sequencing coverage 1030 (inner band).

The genome of the wild type strain of *G. sulfurreducens* consists of a single circular chromosome of 3,814,139 base pairs (bp) and a total of 3466 predicted protein-encoding open reading frames (Methë, B. A., et al., 2003). FIG. 15 is a graphical representation 1000 of the results of whole genome sequencing (SOLEXA®, Illumina, San Diego, Calif.) of the *Geobacter sulfurreducens* strain KN400 showing the positions (kb) of non-synonymously mutated, synonymously mutated and deleted open reading frames (ORFs) 1010 (outer band), the numbers of single nucleotide polymorphisms (SNPs) at positions in open reading frames 1020 (middle band) and the fold sequencing coverage 1030 (inner band). The majority of the ORFs are either deleted, non-synonymously mutated, or synonymously mutated. Overall, about 6% of the genome was deleted.

In general, there are many mutations found in the genome of strain KN400: 11,229 single nucleotide polymorphisms in genes, 34% mutated genes and 22% mutated proteins. Overall, some regions of the chromosome are more heavily mutated than others: energy-related, cell envelope, cytochromes, sensors, and transport proteins. Genes related to DNA and protein synthesis were mutated less often. There are mutations in proteins that fix mutations, as well as mutations that might generate errors.

Example 5

Further Phenotypic Characterization

Strain KN400 was able to produce an amount of electrical current equivalent to that produced by the wild type DL1 strain although having about half the amount of total protein. Biofilms that produced 10 mA in a fuel cell poised by potentiostat at +300 mV were scraped and analyzed. The results are provided in Table 3, below.

TABLE 3

Strain KN400 Has Reduced Total Protein

| Strain | Total Protein (mg/electrode) | Total Protein (mg/cm$^2$) |
| --- | --- | --- |
| KN400 | 1.74 | 0.027 |
| DL1 (WT) | 3.71 | 0.057 |

KN400 exhibited several characteristics suggesting that it was better adapted for biofilm formation. Transmission electron micrographs of KN400 grown in acetate–fumarate medium indicated that KN400 had many more pili than typically seen in DL1 grown under identical conditions (Reguera, G., et al., 2005, Extracellular electron transfer via microbial nanowires, *Nature*, 435(7045): 1098-101).

Figure 16:
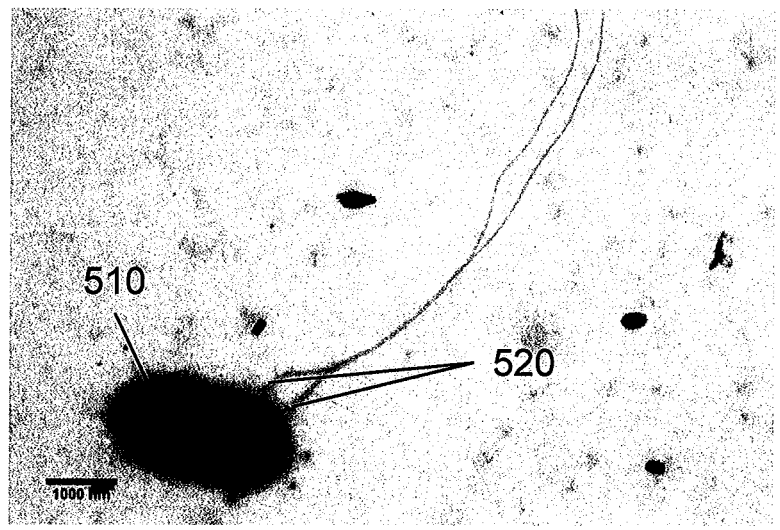
FIG. 16 is a transmission electron micrograph image of a strain KN400 bacterium 510 and lateral flagella 520. The scale bar indicates a length of 1 μm.

In addition to pili, strain KN400 was motile under all growth conditions and exhibited flagella. FIG. 16 is a transmission electron micrograph image of a strain KN400 bacterium 510 and lateral flagella 520. The scale bar indicates a length of 1 μm. In contrast, strain DL1 is non-motile, and flagella have not been previously reported. In addition to providing motility, it has been noted that in other organisms that flagella are important in attachment to surfaces and biofilm formation. If the flagella of strain KN400 have a similar function, the flagella could aid in the development of a superior anode biofilm. The lateral positioning of the flagellum in strain KN400 is consistent with that previously observed in *Geobacter metallireducens*, which specifically expresses flagella when growing on insoluble electron acceptors.

Figure 17:
FIG. 17 is an image of the result of Western blot analysis with an antibody specific for PilA, the structural pilin protein, demonstrating that electrode-grown the KN400 strain had substantially more pilin per mg of cell protein than the DL1 wild-type strain, where the lanes show the size markers ("M"), KN400 proteins ("KN400"), and DL1 proteins ("DL1"), respectively, and the arrow indicates the position of the PilA band.

Western blot analysis with an antibody specific for PilA, the structural pilin protein, confirmed that electrode-grown KN400 had substantially more pilin per mg of cell protein than DL1. FIG. 17 is an image of the result of Western blot analysis with an antibody specific for PilA, the structural pilin protein, demonstrating that electrode-grown the KN400 strain had substantially more pilin per mg of cell protein than the DL1 wild-type strain, where the lanes show the size markers ("M"), KN400 proteins ("KN400"), and DL1 proteins ("DL1"), respectively, and the arrow indicates the position of the PilA band. The increased amount of pilin per mg of cell protein is significant because pili have been implicated in the long-range electron transfer through anode biofilms of *G. sulfurreducens*. Not only are the pili electrically conductive, but they are also required for the development of the thick anode biofilms required for high density current production by *G. sulfurreducens*.

Figures 18A, 18B:
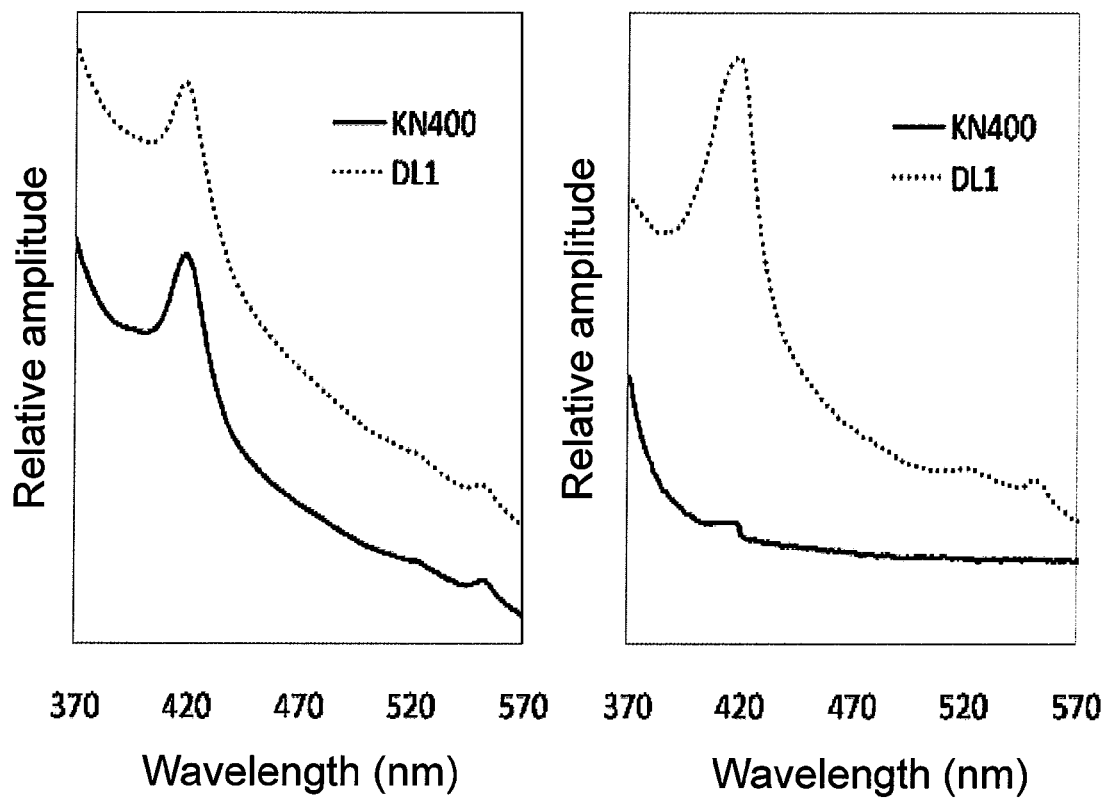
FIG. 18A is a graphical representation of dithionite-reduced minus air oxidized difference spectra of whole cells, indicating that the total c-type cytochrome content of the KN400 strain (solid line) was comparable to that of DL1 wild type strain (dotted line).
FIG. 18B is a graphical representation of dithionite-reduced minus air oxidized difference spectra of preparations of outer-surface proteins from the same quantity of cells, indicating that the c-type cytochromes were much less abundant in the KN400 strain (solid line) than in the DL1 wild type strain (dotted line).

In addition to pili, outer-surface c-type cytochromes are also considered to be important components for electron transfer to electrodes. Dithionite-reduced minus air oxidized difference spectra of whole cells suggested that the total cytochrome content of KN400 was comparable to that of DL1. FIG. 18A is a graphical representation of dithionite-reduced minus air oxidized difference spectra of whole cells, indicating that the total c-type cytochrome content of the KN400 strain (solid line) was comparable to that of DL1 wild type strain (dotted line). FIG. 18B is a graphical representation of dithionite-reduced minus air oxidized difference spectra of preparations of outer-surface proteins from the same quantity of cells, indicating that the c-type cytochromes were much less abundant in the KN400 strain (solid line) than in the DL1 wild type strain (dotted line).

Heme-staining of SDS PAGE preparations of outer-surface proteins indicated that there was a generalized decrease in all of the outer surface c-type cytochromes typically found in DL1. These results suggest that the increased current-producing capacity of strain KN400 could not be attributed to an over-expression of specific outer surface cytochromes.

Exopolysaccharide can significantly influence bacterial adhesion onto solid substratum surfaces, which is recognized as the initial stage in biofilm formation, because the Exopolysaccharide covering on a cell surface alters the physicochemical characteristics of the surface such as charge, hydrophobicity and the polymeric property. The amount of large molecular-weight exopolysaccharide in the KN400 anode biofilms similar to those described above that were analyzed for protein and cell numbers was 0.54±0.04 μg/cm$^2$, which was about half that in the DL1 anode biofilm, 0.91±0.09 μg/cm$^2$. This is comparable to the differences observed in cell protein in the two biofilms.

Figures 19, 21:
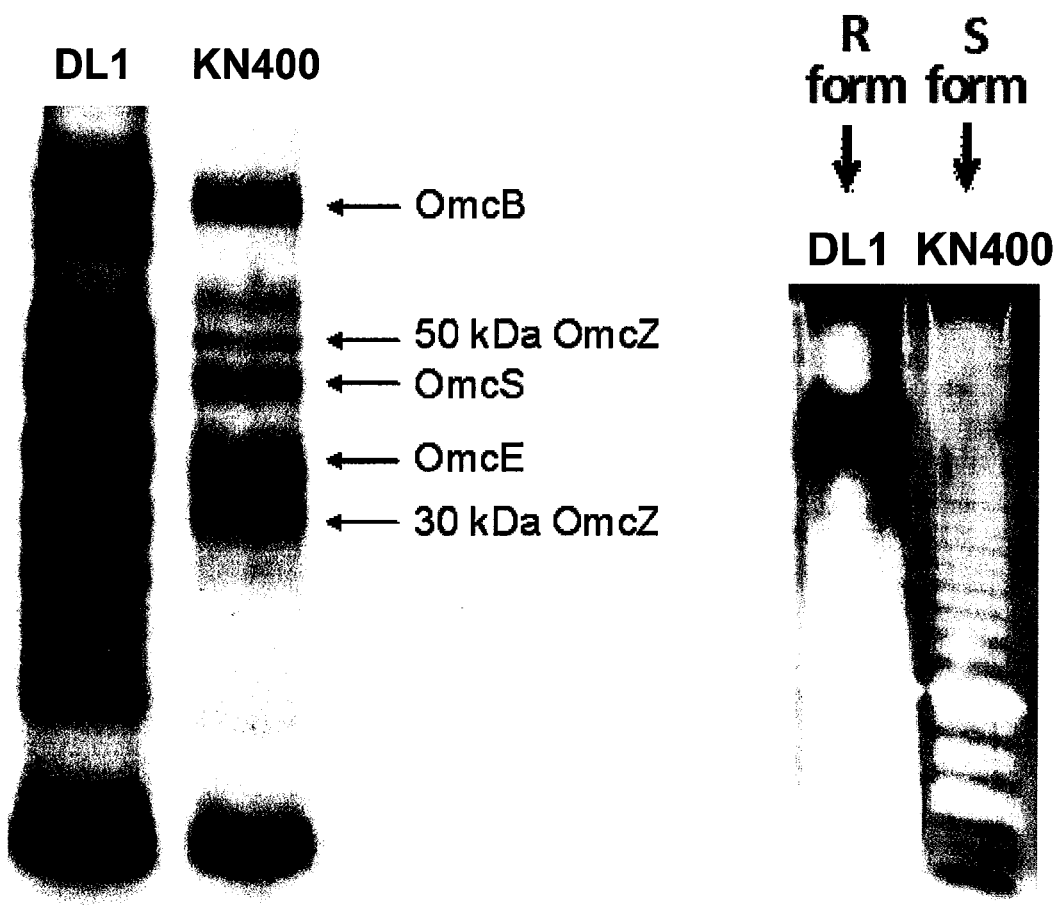
FIG. 19 is an image of the result of gel electrophoresis of outer membrane proteins of the DL1 wild type strain ("WT") and strain KN400, showing the positions of OmcB, 50 kDa OmcZ, OmcS, OmcE, and 30 kDa OmcZ. Exponential phase biofilms that produced 10 mA at ±300 mV were scraped and analyzed. The total heme content of strain KN400 was as low as less than one third of that of the wild type strain.
FIG. 21 is an image of the result of SDS-PAGE analysis and silver staining of lipopolysaccharides (LPS) that were extracted using the hot phenol method. The rough-form LPS ("R form") of the DL1 wild type strain was changed to the smooth-form LPS ("S form") in strain KN400.

FIG. 19 is an image of the result of gel electrophoresis of outer membrane proteins of the DL1 wild type strain ("WT") and strain KN400, showing the positions of OmcB, 50 kDa OmcZ, OmcS, OmcE, and 30 kDa OmcZ. Exponential phase biofilms that produced 10 mA at +300 mV in a potentiostat poised microbial fuel cell were scraped and analyzed. The total heme content of strain KN400 was as low as less than one third of that of the wild type strain.

Figure 20:
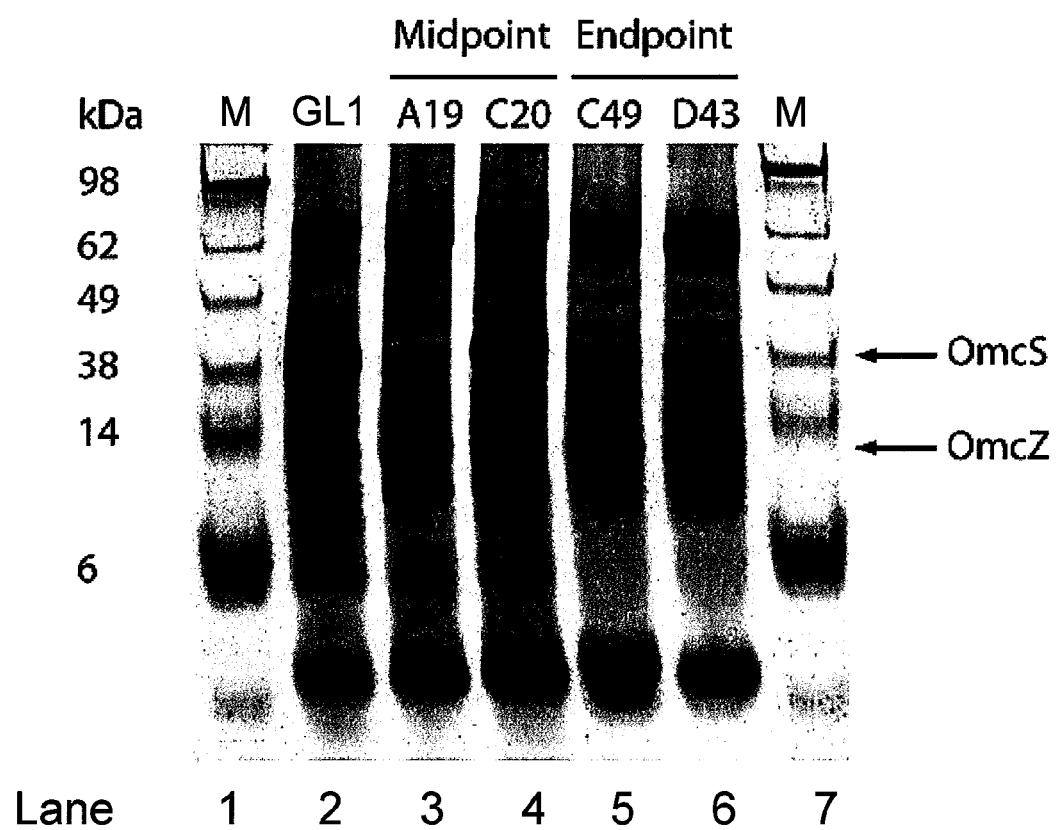
FIG. 20 is an image of the result of gel electrophoresis of outer membrane c-type cytochrome proteins of the DL1 wild type strain ("WT," lane 2), midpoint replicates A19 (lane 3), and C20 (lane 4), and endpoint replicates C49 (lane 5) and D43 (lane 6). Size standard markers are in lanes 1 and 7 ("M"), and the arrows indicate the positions of OmcS and OmcZ.

The cytochrome content of the bacterial outer membrane is lower in the adapted strains than that of the DL1 wild type strain. FIG. 20 is an image of the result of gel electrophoresis of outer membrane c-type cytochrome proteins of the DL1 wild type strain ("WT," lane 2), midpoint replicates A19 (lane 3), and C20 (lane 4), and endpoint replicates C49 (lane 5) and D43 (lane 6). Size standards are in lanes 1 and 7, and the arrows indicate the positions of OmcS and OmcZ.

FIG. 21 is an image of the result of SDS-PAGE analysis and silver staining of lipopolysaccharides (LPS) that were extracted using the hot phenol method. The rough-form LPS ("R form") of the DL1 wild type strain was changed to the smooth-form LPS ("S form") in strain KN400.

The changes in outer surface components were associated with a greater propensity for strain KN400 to stick to surfaces than strain DL1. When grown with fumarate as the electron acceptor KN400 cells were clumpy and adhered strongly to the glass surface of the culture tubes KN400 colonized graphite or glass coupons suspended in the medium much more extensively than DL1 (Table 4, below).

TABLE 4

| KN400 (Cell density, cells/m$^2$) | | DL1 (Cell density, cells/m$^2$) | |
|---|---|---|---|
| Graphite Coupon | Glass Coupon | Graphite Coupon | Glass Coupon |
| $40.0 \pm 11.7 \times 10^{10}$ | $44.9 \pm 13.7 \times 10^{10}$ | $8.2 \pm 2.4 \times 10^{10}$ | $3.5 \pm 3.4 \times 10^{10}$ |
| Culture Tube (OD$_{580}$ after 1% crystal violet staining) | | Culture Tube (OD$_{580}$ after 1% crystal violet staining) | |
| $2.23 \pm 0.08$ | | $0.20 \pm 0.04$ | |

Overall, the characteristics that were examined included growth in non-cathode limited ministacks, growth in poised potential fuel cell systems, biofilm structure of ministacks and poised potential systems, electrochemical characteristics, cytochrome content, growth utilizing other electron acceptors, outer surface proteins, motility and cellular appendages. The tests and the results from comparisons of strain KN400 and the DL1 wild type strain are summarized in Table 5 below.

TABLE 5

Comparison of Characteristics

| Characteristic | Test Type | DL1 Wild Type Strain | Strain KN400 |
|---|---|---|---|
| Maximum Current Density | Non-cathode limited Fuel Cell | $1.4 \pm 0.2$ A/m$^2$ (mean $\pm$ STD n = 3) | $7.4 \pm 0.1$ A/m$^2$ (mean $\pm$ STD n = 3) |
| Midpoint Potential | Cyclic Voltammetry Scan | −181 mV | −150 mV |
| Attachment | Crystal Violet Assay | 0.196 | 2.235 (11 fold increase relative to DL1) |
| Motility | Soft Agar Plate | No | Yes |
| Flagella Present | Electron Microscopy | No | Yes |
| Filaments (Pili) | Electron Microscopy | Some | Many times more than observed in DL1 |
| Outer Membrane Cytochrome Content | Heme stain of protein gel | | 40% reduction relative to DL1 |
| Fe(III) oxide Reduction | Growth Curve | | 10 fold increase relative to DL1 |
| Fumarate Reduction | Growth Curve | 5.8 hr generation time | 9.8 hr generation time |
| Biofilm Conductivity | Impedance Spectroscopy | | 2.5 fold increase relative to DL1 |
| Biofilm Capacitance | Impedance Spectroscopy | | 2.5 fold increase relative to DL1 |
| Cells in Biofilm at same level of current | Potentiostat grown fuel cell | | 20% of DL1 value (indicated much greater efficiency per cell) |

Example 6

Deposit of Adapted *Geobacter* Strain

The isolated *Geobacter sulfurreducens* strain KN400 was deposited on Aug. 5, 2009, on behalf of the University of Massachusetts, 225 Franklin Street, Boston, Mass. 02110, U.S., at the American Type Culture Collection, P.O. Box 1549, Manassas, Va. 20108, U.S., under Accession No. PTA-10251 (PCA: KN400). The deposit has been made pursuant to, and in satisfaction of, the requirements of the Budapest Treaty on the International Recognition of the Deposit of Microorganisms for the Purposes of Patent Procedure.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

Unless otherwise defined, all technical and scientific terms used herein have the same meaning as commonly understood by one of ordinary skill in the art to which this invention belongs. In the case of inconsistencies, the present disclosure, including definitions, will control.

What is claimed is:

1. A microbial fuel cell comprising:
   a housing having an anode chamber and a cathode chamber;
   an anode disposed in an anaerobic environment within the anode chamber and electrically connected to an anode terminal;
   a strain of electricigenic Geobacter sulfurreducens strain KN400, deposited under ATCC Accession No. PTA-10251, disposed in the anaerobic environment within the anode chamber;

a cathode disposed in an aerobic environment within the cathode chamber and electrically connected to a cathode terminal; and a semi-permeable barrier that provides ionic communication between the anode chamber and the cathode chamber.

2. The microbial fuel cell of claim 1, wherein an aqueous solution is in contact with the anode within the anode chamber, said aqueous solution comprising an organic compound that the electricigenic *Geobacter sulfurreducens* strain KN400 can oxidize.

3. The microbial fuel cell of claim 2 wherein the aqueous solution comprises waste water of household, agricultural, or industrial origin.

4. A method of producing a modified electricigenic *Geobacter sulfurreducens* strain KN400, deposited under ATCC Accession No. PTA-10251, the method comprising the steps of:
   a. providing an aliquot of electricigenic *Geobacter sulfurreducens* microbial cells having a first capability to generate electricity in a fuel cell;
   b. providing a sterile microbial fuel cell having an anode, a cathode, an anode chamber in electrical communication through a proton exchange membrane with a cathode chamber and a suitable growth medium for the aliquot of electricigenic *Geobacter sulfurreducens* microbial cells;
   c. placing the aliquot of electricigenic *Geobacter sulfurreducens* microbial cells in the anode chamber of the microbial fuel cell;
   d. maintaining a selected potential difference between the anode and the cathode of the microbial fuel cell using a potentiostat;
   e. measuring the amplitude of the current flowing between the anode and the cathode;
   f. removing an aliquot of electricigenic *Geobacter sulfurreducens* microbial cells from the anode chamber when the current flowing between the anode and the cathode reaches a criterion current amplitude; and
   g. repeating steps a-f M times, using said aliquot of electricigenic *Geobacter sulfurreducens* microbial cells removed in step f in place of said aliquot of electricigenic *Geobacter sulfurreducens* microbial cells recited in step a in each of the M repetitions after the first sequence of steps a-f, which aliquot of electricigenic *Geobacter sulfurreducens* microbial cells removed in step f is placed in a different fuel cell than the one from which it was removed, where M is an integer from 5 to 50 inclusive thereby producing a modified electricigenic *Geobacter sulfurreducens* strain KN400.

5. The method of claim 4 wherein the microbial fuel cell is a flow-through fuel cell that is not cathode limited.

6. The method of claim 4 wherein the selected potential difference is −400 mV.

7. The method of claim 4 wherein the selected potential difference is +300 mV.

8. The method of claim 4 wherein the criterion current amplitude is 10 mA.

9. An isolated culture comprising a modified electricigenic *Geobacter sulfurreducens* strain KN400, deposited under ATCC Accession No. PTA-10251, said modified electricigenic *Geobacter sulfurreducens* strain KN400 microbial cells produced by a method comprising the steps of:
   a. providing an aliquot of electricigenic *Geobacter sulfurreducens* microbial cells having a first capability to generate electricity in a fuel cell;
   b. providing a sterile microbial fuel cell having an anode, a cathode, an anode chamber in electrical communication through a proton exchange membrane with a cathode chamber and a suitable growth medium for the aliquot of electricigenic *Geobacter sulfurreducens* microbial cells;
   c. placing the aliquot of electricigenic *Geobacter sulfurreducens* microbial cells in the anode chamber of the microbial fuel cell;
   d. maintaining a selected potential difference between the anode and the cathode of the microbial fuel cell using a potentiostat;
   e. measuring the amplitude of the current flowing between the anode and the cathode;
   f. removing an aliquot of electricigenic *Geobacter sulfurreducens* microbial cells from the anode chamber when the current flowing between the anode and the cathode reaches a criterion current amplitude; and
   g. repeating steps a-f M times, using said aliquot of electricigenic *Geobacter sulfurreducens* microbial cells removed in step f in place of said aliquot of electricigenic *Geobacter sulfurreducens* microbial cells recited in step a in each of the M repetitions after the first sequence of steps a-f, which aliquot of electricigenic *Geobacter sulfurreducens* microbial cells removed in step f is placed in a different fuel cell than the one from which it was removed, where M is an integer from 5 to 50 inclusive thereby producing a modified electricigenic *Geobacter sulfurreducens* strain KN400 that is specifically adapted for the production of electrical current in said microbial fuel cell and that exhibits an improved capability to generate electricity in a fuel cell as compared to said first capability to generate electricity in a fuel cell.

10. The isolated culture of claim 9, wherein the selected potential difference in step d is that of an anode poised at −400 mV vs. an Ag/AgCl electrode.

11. The isolated culture of claim 9, wherein the selected potential difference in step d is that of an anode poised at +300 mV referenced to an Ag/AgCl electrode.

* * * * *